(12) United States Patent
Janda et al.

(10) Patent No.: US 6,472,147 B1
(45) Date of Patent: Oct. 29, 2002

(54) METHODS FOR DISPLAY OF HETERODIMERIC PROTEINS ON FILAMENTOUS PHAGE USING PVII AND PIX, COMPOSITIONS, VECTORS AND COMBINATORIAL LIBRARIES

(75) Inventors: Kim D. Janda, La Jolla; Peter Wirsching, Del Mar; Richard A. Lerner, La Jolla; Changshou Gao, San Diego, all of CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/318,786

(22) Filed: May 25, 1999

(51) Int. Cl.[7] .................... C12Q 1/70; C12P 21/04; C07K 16/00
(52) U.S. Cl. .................. 435/5; 435/69.7; 435/320.1; 435/DIG. 23; 435/DIG. 24; 530/387.1
(58) Field of Search .................... 435/5, 6, 4, 7.1, 435/DIG. 1, DIG. 23, DIG. 24, 69.1, 69.7, 320.1; 424/162.1, 93.6; 530/300, 350, 387.1

(56) References Cited

U.S. PATENT DOCUMENTS

| | | |
|---|---|---|
| 5,871,974 A | 2/1999 | Huse |
| 5,985,588 A | 11/1999 | Breitling et al. |
| 6,027,930 A | 2/2000 | Borrebaeck |
| 6,027,933 A | 2/2000 | Huse |
| 6,054,312 A | 4/2000 | LaRocca et al. |
| 6,127,132 A | 10/2000 | Breitling et al. |
| 6,172,197 B1 | 1/2001 | McCafferty et al. |

OTHER PUBLICATIONS

Gao, et al., Making artificial antibodies: A format for phage display of combinatorial heterodimeric arrays, 1999, *Proc. Natl. Acad. Sci. USA*, 96:6025–6030.

Madison–Antenucci, et al., Translation limits synthesis of an assembly–initiating coat protein of filamentous phage IKe, 1998, *J. Bacteriology*, 180(3):464–472.

*Primary Examiner*—Padmashri Ponnaluri
(74) *Attorney, Agent, or Firm*—Thomas Fitting; Emily Holmes

(57) ABSTRACT

The invention describes the display of exogenous polypeptides on filamentous phage using a fusion between the exogenous polypeptide and phage pVII or pIX proteins. In particular, phage particles and phagemid vectors are described for expression and display of heterodimeric proteins such a antibody Fv heterodimers in combinatorial libraries, and uses thereof.

5 Claims, 9 Drawing Sheets

PCP hapten

GNC hapten

SEQUENCE LISTING

<160> NUMBER OF SEQ ID NOS: 39

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 1
ctatccatgg caatggagca ggtcgcggat ttc    33

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 2
atttagctag cttatttgtc atcgtcatct tgtagtctc tttgaccccc agcgattat    59

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 3
ctatccatgg cagactacaa agatgacgat gacaaaatgg agcaggtcgc ggatttc    57

<210> SEQ ID NO 4

```
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 4
gatttagcta gcttattatc tttgaccccc agcgattat                       39

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 5
ctatccatgg caatgagtgt tttagtgtat tct                             33

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Primer

<400> SEQUENCE: 6
atttagctag cttatttgtc atcgtcatct ttgtagtctg aggaagtttc cattaaacg    59

<210> SEQ ID NO 7
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 7
ctatccatgg cagactacaa agatgacgat gacaaaatga gtgttttagt gtattct      57

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 8
gatttagcta gcttattatg aggaagtttc cattaaacg                       39

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 9
gcctacggca gccgctggat tgttattact                                 30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
```

-continued

```
gccagaacca ccaccagaga cagtgaccag                                              30

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 11
gccagaacca ccaccagaga cggtgactga ggttcc                                       36

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 12
gccagaacca ccaccagatg aggaaacggt gaccgt                                       36

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
gctatcgcga ttgctgtggc actggctggt                                              30

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 14
ggagccgccg ccgccagaat cagcccgttt gatttc                                       36

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 15
ggagccgccg ccgccagaat cagtccgttt caactc                                       36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 16
ggagccgccg ccgccagaga ccaggccccc gaggcc                                       36

<210> SEQ ID NO 17
<211> LENGTH: 38
<212> TYPE: DNA
```

<213> ORGANISM: Artificial Sequence
<220> FEATURE:
<223> OTHER INFORMATION: Description of Artificial Sequence: Primer

<400> SEQUENCE: 17
tctggtggtg gttctggcat ggagcaggtc gcgatttc        38

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 18
tctggcggcg gcggctccat gagtgtttta gtgtattct        39

<210> SEQ ID NO 19
<211> LENGTH: 3379
<212> TYPE: DNA
<213> ORGANISM: Artificial Sequence
<220> FEATURE:
<223> OTHER INFORMATION: Description of Artificial Sequence: Vector

<400> SEQUENCE: 19
gggaaattgt aagcgttaat attttgttaa aattcgcgtt aaattttttgt taaatcagct      60
cattttttaa ccaataggcc gaaatcggca aaatccctta taaatcaaaa gaatagaccg     120
agatagggtt gagtgttgtt ccagtttgga acaagagtcc actattaaag aacgtggact     180
ccaacgtcaa agggcgaaaa accgtctatc agggcgatgg cccactacgt gaaccatcac     240
cctaatcaag ttttttgggg tcgaggtgcc gtaaagcact aaatcggaac cctaaaggga     300
gcccccgatt tagagcttga cggggaaagc cggcgaacgt ggcgagaaag gaagggaaga     360
aagcgaaagg agcgggcgct agggcgctgg caagtgtagc ggtcacgctg cgcgtaacca     420
ccacacccgc cgcgcttaat gcgccgctac agggcgcgtc aggtggcact tttcggggaa     480
atgtgcgcgg aacccctatt tgtttatttt tctaaataca ttcaaatatg tatccgctca     540
tgagacaata accctgataa atgcttcaat aatattgaaa aaggaagagt atgagtattc     600
aacatttccg tgtcgccctt attcccttttt ttgcggcatt ttgccttcct gttttttgctc     660
acccagaaac gctggtgaaa gtaaaagatg ctgaagatca gttgggtgca cgagtgggtt     720
acatcgaact ggatctcaac agcggtaaga tccttgagag ttttcgcccc gaagaacgtt     780
ttccaatgat gagcactttt aaagttctgc tatgtggcgc ggtattatcc cgtattgacg     840
ccgggcaaga gcaactcggt cgccgcatac actattctca gaatgacttg gttgagtact     900
caccagtcac agaaaagcat cttacggatg gcatgacagt aagagaatta tgcagtgctg     960
ccataaccat gagtgataac actgcggcca acttacttct gacaacgatc ggaggaccga    1020
aggagctaac cgcttttttg cacaacatgg gggatcatgt aactcgcctt gatcgttggg    1080
aaccggagct gaatgaagcc ataccaaacg acgagcgtga ccacgatg cctgtagcaa    1140
tggcaacaac gttgcgcaaa ctattaactg gcgaactact tactctagct tcccggcaac    1200
aattaataga ctggatggag gcggataaag ttgcaggacc acttctgcgc tcggcccttc    1260
cggctggctg gtttattgct gataaatctg gagccggtga gcgtgggtct cgcggtatca    1320
ttgcagcact ggggccagat ggtaagccct cccgtatcgt agttatctac acgacgggga    1380
gtcaggcaac tatggatgaa cgaaatagac agatcgctga gataggtgcc tcactgatta    1440
agcattggta actgtcagac caagtttact catatatact ttagattgat ttaaaacttc    1500

```
atttttaatt taaaaggatc taggtgaaga tcctttttga taatctcatg accaaaatcc   1560
cttaacgtga gttttcgttc cactgagcgt cagaccccgt agaaaagatc aaaggatctt   1620
cttgagatcc ttttttctg cgcgtaatct gctgcttgca acaaaaaaa ccaccgctac     1680 cagcggtggt ttgtttgccg gatcaagagc taccaactct ttttccgaag gtaactggct   1740
tcagcagagc gcagatacca aatactgtcc ttctagtgta gccgtagtta ggccaccact   1800
tcaagaactc tgtagcaccg cctacatacc tcgctctgct aatcctgtta ccagtggctg   1860
ctgccagtgg cgataagtcg tgtcttaccg ggttggactc aagacgatag ttaccggata   1920
aggcgcagcg gtcgggctga acggggggtt cgtgcacaca gcccagcttg gagcgaacga   1980
cctacaccga actgagatac ctacagcgtg agctatgaga agcgccacg cttcccgaag    2040 ggagaaaggc ggacaggtat ccggtaagcg gcagggtcgg aacaggagag cgcacgaggg   2100
agcttccagg gggaaacgcc tggtatcttt atagtcctgt cgggtttcgc cacctctgac   2160
ttgagcgtcg attttgtga tgctcgtcag gggggcggag cctatggaaa aacgccagca    2220
acgcggcctt tttacggttc ctggcctttt gctggccttt tgctcacatg ttctttcctg   2280
cgttatcccc tgattctgtg gataaccgta ttaccgcctt tgagtgagct gataccgctc   2340
gccgcagccg aacgaccgag cgcagcgagt cagtgagcga ggaagcggaa gagcgcccaa   2400
tacgcaaacc gcctctcccc gcgcgttggc cgattcatta atgcagggta cccgataaaa   2460
gcggcttcct gacaggaggc cgttttgttt tgcagcccac ctctggcacg acaggttttcc  2520 cgactggaaa gcgggcagtg agcgcaacgc aattaatgtg agttagctca ctcattaggc   2580 acccaggct ttacactta tgcttccggc tcgtatgttg tgtggaattg tgagcggata     2640
acaattgaat tcaggaggaa tttaaaatga atacctatt gcctacggca gccgctggat    2700
tgttattact cgcggcccag ccggccatgg caaagcttgg atccgatatc catatgggcc   2760 tcggggcct ggtcgactac aaagatgacg atgacaaata gactagtggc caggagggtg    2820
gtggctctga gggtggcggt tctgagggtg gcggctctga gggaggcggt tccggtggtg   2880
gctctggttc cggtgatttt gattatgaaa agatggcaaa cgctaataag ggggctatga   2940
ccgaaaatgc cgatgaaaac gcgctacagt ctgacgctaa aggcaaactt gattctgtcg   3000
ctactgatta cggtgctgct atcgatggtt tcattggtga cgtttccggc cttgctaatg   3060
gtaatggtgc tactggtgat tttgctggct ctaattccca aatggctcaa gtcggtgacg   3120
gtgataattc acctttaatg aataatttcc gtcaatattt accttccctc cctcaatcgg   3180
ttgaatgtcg ccctttgtc tttagcgctg gtaaaccata tgaattttct attgattgtg    3240
acaaaataaa cttattccgt ggtgtctttg cgtttctttt atatgttgcc acctttatgt   3300
atgtattttc tacgtttgct aacatactgc gtaataagga gtcttaagct agctaattaa   3360
tttaagcggc cgcagatct                                                3379
```

<210> SEQ ID NO 20
<211> LENGTH: 3450
<212> TYPE: DNA
<213> ORGANISM: Artificial Sequence
<220> FEATURE:
<223> OTHER INFORMATION: Description of Artificial Sequence: Vector

<400> SEQUENCE: 20

```
gggaaattgt aagcgttaat attttgttaa aattcgcgtt aaattttgt taaatcagct     60 cattttttaa ccaataggcc gaaatcggca aaatccctta taaatcaaaa gaatagaccg   120
```

-continued

| | | | | |
|---|---|---|---|---|
| agatagggtt | gagtgttgtt | ccagtttgga | acaagagtcc | actattaaag aacgtggact | 180 |
| ccaacgtcaa | agggcgaaaa | accgtctatc | agggcgatgg | cccactacgt gaaccatcac | 240 |
| cctaatcaag | ttttttgggg | tcgaggtgcc | gtaaagcact | aaatcggaac cctaaaggga | 300 |
| gcccccgatt | tagagcttga | cggggaaagc | cggcgaacgt | ggcgagaaag aagggaaga | 360 |
| aagcgaaagg | agcgggcgct | agggcgctgg | caagtgtagc | ggtcacgctg cgcgtaacca | 420 |
| ccacacccgc | cgcgcttaat | gcgccgctac | agggcgcgtc | aggtggcact tttcggggaa | 480 |
| atgtgcgcgg | aaccCctatt | tgtttatttt | tctaaataca | ttcaaatatg tatccgctca | 540 |
| tgagacaata | accctgataa | atgcttcaat | aatattgaaa | aggaagagt atgagtattc | 600 |
| aacatttccg | tgtcgccctt | attcccttTT | ttgcggcatt | ttgccttcct gttttTgctc | 660 |
| acccagaaac | gctggtgaaa | gtaaaagatg | ctgaagatca | gttgggtgca cgagtgggtt | 720 |
| acatcgaact | ggatctcaac | agcggtaaga | tccttgagag | ttttcgcccc gaagaacgtt | 780 |
| ttccaatgat | gagcactttt | aaagttctgc | tatgtggcgc | ggtattatcc cgtattgacg | 840 |
| ccgggcaaga | gcaactcggt | cgccgcatac | actattctca | gaatgacttg gttgagtact | 900 |
| caccagtcac | agaaaagcat | cttacggatg | gcatgacagt | aagagaatta tgcagtgctg | 960 |
| ccataaccat | gagtgataac | actgcggcca | acttacttct | gacaacgatc ggaggaccga | 1020 |
| aggagctaac | cgcttttttg | cacaacatgg | ggatcatgt | aactcgcctt gatcgttggg | 1080 |
| aaccggagct | gaatgaagcc | ataccaaacg | acgagcgtga | caccacgatg cctgtagcaa | 1140 |
| tggcaacaac | gttgcgcaaa | ctattaactg | gcgaactact | tactctagct tcccggcaac | 1200 |
| aattaataga | ctggatggag | gcggataaag | ttgcaggacc | acttctgcgc tcggcccttc | 1260 |
| cggctggctg | gtttattgct | gataaatctg | gagccggtga | gcgtgggtct cgcggtatca | 1320 |
| ttgcagcact | ggggccagat | ggtaagccct | cccgtatcgt | agttatctac acgacgggga | 1380 |
| gtcaggcaac | tatggatgaa | cgaaatagac | agatcgctga | gataggtgcc tcactgatta | 1440 |
| agcattggta | actgtcagac | caagtttact | catatatact | ttagattgat ttaaaacttc | 1500 |
| atttttaatt | taaaaggatc | taggtgaaga | tcctttttga | taatctcatg accaaaatcc | 1560 |
| cttaacgtga | gttttcgttc | cactgagcgt | cagaccccgt | agaaaagatc aaaggatctt | 1620 |
| cttgagatcc | tttttttctg | cgcgtaatct | gctgcttgca | aacaaaaaaa ccaccgctac | 1680 |
| cagcggtggt | ttgtttgccg | gatcaagagc | taccaactct | ttttccgaag gtaactggct | 1740 |
| tcagcagagc | gcagatacca | aatactgtcc | ttctagtgta | gccgtagtta ggccaccact | 1800 |
| tcaagaactc | tgtagcaccg | cctacatacc | tcgctctgct | aatcctgtta ccagtggctg | 1860 |
| ctgccagtgg | cgataagtcg | tgtcttaccg | ggttggactc | aagacgatag ttaccggata | 1920 |
| aggcgcagcg | gtcgggctga | acggggggtt | cgtgcacaca | gcccagcttg gagcgaacga | 1980 |
| cctacaccga | actgagatac | ctacagcgtg | agctatgaga | aagcgccacg cttcccgaag | 2040 |
| ggagaaaggc | ggacaggtat | ccggtaagcg | gcagggtcgg | aacaggagag cgcacgaggg | 2100 |
| agcttccagg | gggaaacgcc | tggtatcttt | atagtcctgt | cgggtttcgc cacctctgac | 2160 |
| ttgagcgtcg | atttttgtga | tgctcgtcag | ggggcggag | cctatggaaa aacgccagca | 2220 |
| acgcggcctt | tttacggttc | ctggcctttt | gctggccttt | tgctcacatg ttctttcctg | 2280 |
| cgttatcccc | tgattctgtg | gataaccgta | ttaccgcctt | tgagtgagct gataccgctc | 2340 |
| gccgcagccg | aacgaccgag | cgcagcgagt | cagtgagcga | ggaagcggaa gagcgcccaa | 2400 |
| tacgcaaacc | gcctctcccc | gcgcgttggc | cgattcatta | atgcagggta cccgataaaa | 2460 |
| gcggcttcct | gacaggaggc | cgttttgttt | tgcagcccac | ctctggcacg acaggtttcc | 2520 |

-continued

```
cgactggaaa gcgggcagtg agcgcaacgc aattaatgtg agttagctca ctcattaggc    2580
accccaggct ttacacttta tgcttccggc tcgtatgttg tgtggaattg tgagcggata    2640
acaattgaat tcaggaggaa tttaaaatga aaaagacagc tatcgcgatt gcagtggcac    2700
tggctggttt cgctaccgtg gcccaggcgg ccgagctcat gcattctaga taattaatta    2760
ggaggaattt aaaatgaaat acctattgcc tacggcagcc gctggattgt tattactcgc    2820
tgcccaacca gccatggccg aggtgcagct gctcgaggga tccactagtg ccaggccgg    2880 ccaggagggt ggtggctctg agggtggcgg ttctgagggt ggcggctctg agggaggcgg    2940
ttccggtggt ggctctggtt ccggtgattt tgattatgaa agatggcaa acgctaataa     3000 ggggctatg accgaaaatg ccgatgaaaa cgcgctacag tctgacgcta aaggcaaact    3060
tgattctgtc gctactgatt acggtgctgc tatcgatggt ttcattggtg acgtttccgg    3120
ccttgctaat ggtaatggtg ctactggtga ttttgctggc tctaattccc aaatggctca    3180
agtcggtgac ggtgataatt cacctttaat gaataatttc cgtcaatatt taccttccct    3240
ccctcaatcg gttgaatgtc gcccttttgt ctttagcgct ggtaaaccat atgaattttc    3300
tattgattgt gacaaaataa acttattccg tggtgtcttt gcgtttcttt tatatgttgc    3360
cacctttatg tatgtatttt ctacgtttgc taacatactg cgtaataagg agtcttaagc    3420
tagctaatta atttaagcgg ccgcagatct                                     3450
```

<210> SEQ ID NO 21
<211> LENGTH: 33
<212> TYPE: PRT
<213> ORGANISM: Artificial Sequence
<220> FEATURE:
<223> OTHER INFORMATION: Description of Artificial Sequence: filamentous
      phage protein

<400> SEQUENCE: 21

Met Glu Gln Val Ala Asp Phe Asp Thr Ile Tyr Gln Ala Met Ile Gln
 1               5                  10                  15

Ile Ser Val Val Leu Cys Phe Ala Leu Gly Ile Ile Ala Gly Gly Gln
            20                  25                  30

Arg

<210> SEQ ID NO 22
<211> LENGTH: 102
<212> TYPE: DNA
<213> ORGANISM: Artificial Sequence
<220> FEATURE:
<223> OTHER INFORMATION: Description of Artificial Sequence: filamentous
      phage nucleotide

<400> SEQUENCE: 22
atggagcagg tcgcggattt cgacacaatt tatcaggcga tgatacaaat ctccgttgta    60
ctttgtttcg cgcttggtat aatcgctggg ggtcaaagat ga                       102

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: filamentous
      phage protein

<400> SEQUENCE: 23

Met Ser Val Leu Val Tyr Ser Phe Ala Ser Phe Val Leu Gly Trp Cys

-continued

```
                 1               5              10              15
Leu Arg Ser Gly Ile Thr Tyr Phe Thr Arg Leu Met Glu Thr Ser Ser
                20              25              30
```

<210> SEQ ID NO 24
<211> LENGTH: 99
<212> TYPE: DNA
<213> ORGANISM: Artificial Sequence
<220> FEATURE:
<223> OTHER INFORMATION: Description of Artificial Sequence: filamentous phage nucleotide

<400> SEQUENCE: 24

```
atgagtgttt tagtgtattc tttcgcctct ttcgttttag gttggtgcct tcgtagtggc      60
attacgtatt ttacccgttt aatggaaact tcctcatga                            99
```

<210> SEQ ID NO 25
<211> LENGTH: 148
<212> TYPE: PRT
<213> ORGANISM: Artificial Sequence
<220> FEATURE:
<223> OTHER INFORMATION: Description of Artificial Sequence: fusion polypeptide

<400> SEQUENCE: 25

```
Asp Ile Gln Met Thr Gln Ser Pro Ser Ser Leu Ser Ala Ser Leu Gly
 1               5              10              15

Glu Arg Val Ser Leu Thr Cys Arg Ala Ser Gln Glu Ile Ser Gly Tyr
                20              25              30

Leu Tyr Trp Leu Gln Gln Lys Pro Asp Gly Thr Ile Lys Arg Leu Ile
            35              40              45

Tyr Ala Ala Ser Thr Leu Asp Ser Gly Val Pro Lys Arg Phe Ser Gly
        50              55              60

Ser Arg Ser Gly Ser Asp Tyr Ser Leu Thr Ile Ser Ser Leu Glu Ser
 65              70              75              80

Glu Asp Phe Ala Asp Tyr Tyr Cys Leu Gln Tyr Ala Ser Tyr Pro Arg
                85              90              95

Thr Phe Gly Gly Gly Thr Lys Val Glu Ile Lys Arg Ala Asp Ser Gly
            100             105             110

Gly Gly Gly Ser Met Ser Val Leu Val Tyr Ser Phe Ala Ser Phe Val
        115             120             125

Leu Gly Trp Cys Leu Arg Ser Gly Ile Thr Tyr Phe Thr Arg Leu Met
    130             135             140

Glu Thr Ser Ser
145
```

<210> SEQ ID NO 26
<211> LENGTH: 456
<212> TYPE: DNA
<213> ORGANISM: Artificial Sequence
<220> FEATURE:
<223> OTHER INFORMATION: Description of Artificial Sequence: nucleotide encoding fusion polypeptide

<400> SEQUENCE: 26

```
gatatccaaa tgacacaatc tccatcctcc ttatctgcct ctctgggaga aagagtcagt      60
ctcacttgtc gggcaagtca ggagattagt ggttacttat actggcttca gcagaaacca    120
gatggaacta ttaaacgcct gatctacgcc gcatccactt tagattctgg tgtcccaaaa    180
aggttcagtg gcagtaggtc tgggtcagat tattctctca ccatcagcag ccttgagtct    240
```

```
gaagattttg cagactatta ctgtctacaa tatgctagtt atcctcggac gttcggtgga      300
ggcaccaagg ttgaaatcaa acgggctgat tctggcggcg gcggctccat gagtgtttta      360
gtgtattctt tcgcctcttt cgttttaggt tggtgccttc gtagtggcat tacgtatttt      420
acccgtttaa tggaaacttc ctcataataa gctagc                                456
```

<210> SEQ ID NO 27
<211> LENGTH: 163
<212> TYPE: PRT
<213> ORGANISM: Artificial Sequence
<220> FEATURE:
<223> OTHER INFORMATION: Description of Artificial Sequence: fusion polypeptide

<400> SEQUENCE: 27

```
Met Ala Glu Val Gln Leu Leu Glu Val Gln Leu Gln Gln Ser Gly Pro
 1               5                  10                  15

Val Leu Val Lys Pro Gly Gly Ser Val Lys Met Ser Cys Lys Ala Ser
            20                  25                  30

Glu Tyr Thr Leu Thr Ser Tyr Leu Phe Gln Trp Val Lys Gln Lys Ser
        35                  40                  45

Gly Gln Gly Leu Glu Trp Ile Gly Tyr Ile Tyr Pro Tyr Asn Gly Gly
    50                  55                  60

Thr Arg Tyr Asn Glu Lys Phe Arg Gly Lys Ala Thr Leu Thr Ser Asp
65                  70                  75                  80

Lys Ser Ser Asn Thr Ala Tyr Leu Glu Leu Ser Ser Leu Thr Ser Glu
                85                  90                  95

Asp Ser Ala Val Tyr Tyr Cys Ala Arg Ser Ser Met Ser Asp Pro Gly
            100                 105                 110

Ala Asn Trp Gly Pro Gly Thr Leu Val Thr Val Ser Gly Gly Gly Gly
        115                 120                 125

Ser Gly Met Glu Gln Val Ala Asp Phe Asp Thr Ile Tyr Gln Ala Met
    130                 135                 140

Ile Gln Ile Ser Val Val Leu Cys Phe Ala Leu Gly Ile Ile Ala Gly
145                 150                 155                 160

Gly Gln Arg
```

<210> SEQ ID NO 28
<211> LENGTH: 501
<212> TYPE: DNA
<213> ORGANISM: Artificial Sequence
<220> FEATURE:
<223> OTHER INFORMATION: Description of Artificial Sequence: nucleotide encoding fusion polypeptide

<400> SEQUENCE: 28

```
atggccgagg tgcagctgct cgaggtccag ctgcaacaat ctggacctgt gctggtaaag      60
cctgggggtt cagtgaaaat gtcctgcaag gcttctgaat acacactcac ttcttatctt      120
tttcagtggg tgaagcagaa gtcagggcag ggccttgagt ggattggata tatttatcct      180
tacaatggtg gtactcggta caatgagaag ttcagaggca aggccacact gacttcagac      240
aagtcctcca acacagccta cttggaactc agcagcctga cctctgaaga ctctgcagtc      300
tattactgtg caagatctag tatgagtgac cccggggcta actggggccc agggactctg      360
gtcactgtct ctggtggtgg tggttctggc atggagcagg tcgcggattt cgacacaatt      420
tatcaggcga tgatacaaat ctccgttgta ctttgtttcg cgcttggtat aatcgctggg      480
```
ggtcaaagat aataagctag c     501

<210> SEQ ID NO 29
<211> LENGTH: 144
<212> TYPE: PRT
<213> ORGANISM: Artificial Sequence
<220> FEATURE:
<223> OTHER INFORMATION: Description of Artificial Sequence: fusion
      polypeptide

<400> SEQUENCE: 29

Val Leu Thr Gln Ser Pro Ala Ile Met Tyr Ala Ser Pro Gly Glu Lys
 1               5                  10                  15

Val Thr Ile Thr Cys Ser Ala Ser Ser Val Ser Tyr Met His Trp
             20                  25                  30

Phe Gln Gln Lys Pro Gly Thr Ser Pro Lys Leu Trp Ile Tyr Ser Thr
             35                  40                  45

Ser Lys Leu Ala Ser Gly Val Pro Ala Arg Phe Ser Gly Ser Gly Ser
         50                  55                  60

Gly Thr Ser Tyr Ser Leu Thr Ile Ser Arg Met Glu Ala Glu Asp Val
 65                  70                  75                  80

Ala Thr Tyr Tyr Cys Gln Gln Arg Ser Ser Tyr Thr Val Thr Phe Gly
                 85                  90                  95

Ala Gly Thr Lys Leu Glu Leu Lys Arg Thr Ser Gly Gly Gly Gly Ser
            100                 105                 110

Met Ser Val Leu Val Tyr Ser Phe Ala Ser Phe Val Leu Gly Trp Cys
            115                 120                 125

Leu Arg Ser Gly Ile Thr Tyr Phe Thr Arg Leu Met Glu Thr Ser Ser
        130                 135                 140

<210> SEQ ID NO 30
<211> LENGTH: 443
<212> TYPE: DNA
<213> ORGANISM: Artificial Sequence
<220> FEATURE:
<223> OTHER INFORMATION: Description of Artificial Sequence: nucleotide
      encoding fusion polypeptide

<400> SEQUENCE: 30
gtgctcaccc agtctccagc aatcatgtat gcatctccag gggagaaggt caccataacc     60
tgcagtgcca gctcaagtgt aagttacatg cactggttcc agcagaagcc aggcacttct    120
cccaaactct ggatttatag cacatccaag ctggcttctg gagtccctgc tcgcttcagt    180
ggcagtggat ctgggacctc ttactctctc acaatcagcc gaatggaggc tgaagatgtt    240
gccacttatt actgccagca aaggagcagt tatacggtca cgttcggtgc tgggaccaag    300
ctggagttga aacggacttc tggcggcggc ggctccatga gtgttttagt gtattctttc    360
gcctctttcg ttttaggttg gtgccttcgt agtggcatta cgtattttac ccgtttaatg    420
gaaacttcct cataataagc tag    443

<210> SEQ ID NO 31
<211> LENGTH: 167
<212> TYPE: PRT
<213> ORGANISM: Artificial Sequence
<220> FEATURE:
<223> OTHER INFORMATION: Description of Artificial Sequence: fusion
      polypeptide

<400> SEQUENCE: 31

Met Ala Glu Val Gln Leu Leu Glu Glu Val Asn Leu Val Glu Ser Gly

```
              1               5              10              15
       Gly Gly Leu Val Lys Pro Gly Ser Leu Lys Leu Ser Cys Ala Ala
                        20              25              30

Ser Gly Phe Thr Phe Ser Ser Tyr Ala Met Ser Trp Val Arg Gln Thr
                    35              40              45

Pro Glu Lys Arg Leu Glu Trp Val Ala Ser Ile Asn Asn Gly Gly Lys
                50              55              60

Ile Tyr Tyr Pro Asp Ser Val Lys Gly Arg Phe Thr Ile Ser Arg Asp
        65              70              75              80

Asn Ala Arg Asn Ile Leu Tyr Leu Gln Met Ser Ser Leu Arg Ser Glu
                        85              90              95

Asp Thr Ala Met Tyr Tyr Cys Val Lys Arg Asp Ser Ser Val Tyr Asp
                       100             105             110

Tyr Ala Met Asp Asn Trp Gly Gln Gly Thr Ser Val Thr Val Ser Ser
                    115             120             125

Gly Gly Gly Gly Ser Gly Met Glu Gln Val Ala Asp Phe Asp Thr Ile
                130             135             140

Tyr Gln Ala Met Ile Gln Ile Ser Val Val Leu Cys Phe Ala Leu Gly
       145             150             155             160

Ile Ile Ala Gly Gly Gln Arg
                       165

<210> SEQ ID NO 32
<211> LENGTH: 513
<212> TYPE: DNA
<213> ORGANISM: Artificial Sequence
<220> FEATURE:
<223> OTHER INFORMATION: Description of Artificial Sequence: nucleotide
      encoding fusion polypeptide

<400> SEQUENCE: 32
atggccgagg tgcagctgct cgaggaagtg aatctggtgg agtctggggg aggcttagtg       60
aagcctggag gtccctgaa  actctcctgt gcagcctctg gattcacttt tagtagttat      120
gccatgtctt gggttcgcca gactccagag aagaggctgg agtgggtcgc atccattaat      180
aatggtggta aaatctacta tccagacagt gtgaagggcc gattcaccat ctccagagat      240
aatgccagga acatcctgta tcttcaaatg agcagtctga ggtctgagga cacggccatg      300
tattactgtg taaaaagaga cagttcggtc tacgactatg ctatggacaa ctggggtcaa      360
ggaacctcag tcaccgtctc ctctggtggt ggtggttctg gcatggagca ggtcgcggat      420
ttcgacacaa tttatcaggc gatgatacaa atctccgttg tactttgttt cgcgcttggt      480
ataatcgctg ggggtcaaag ataataagct agc                                   513

<210> SEQ ID NO 33
<211> LENGTH: 151
<212> TYPE: PRT
<213> ORGANISM: Artificial Sequence
<220> FEATURE:
<223> OTHER INFORMATION: Description of Artificial Sequence: fusion
      polypeptide

<400> SEQUENCE: 33

Asp Ile Gly Leu Thr Gln Ser Pro Ala Ser Leu Ala Val Ser Leu Gly
        1               5              10              15

Gln Arg Ala Thr Ile Ser Cys Arg Ala Ser Lys Ser Val Ser Thr Ser
                        20              25              30

Gly Tyr Asn Tyr Met His Trp Tyr Gln Gln Lys Pro Gly Gln Pro Pro
```

-continued

```
                35                  40                  45
Lys Leu Leu Ile Tyr Leu Ala Ser Asn Leu Ala Ser Gly Val Pro Ala
        50                  55                  60

Arg Phe Ser Gly Ser Gly Ser Gly Thr Asp Phe Thr Leu Asn Ile His
 65                  70                  75                  80

Pro Val Glu Glu Asp Ala Ala Thr Tyr Tyr Cys Leu Tyr Ser Arg
                 85                  90                  95

Glu Phe Pro Pro Trp Thr Phe Gly Gly Gly Thr Lys Leu Glu Ile Lys
                100                 105                 110

Arg Ser Gly Gly Gly Ser Met Ser Val Leu Val Tyr Ser Phe Ala
            115                 120                 125

Ser Phe Val Leu Gly Trp Cys Leu Arg Ser Gly Ile Thr Tyr Phe Thr
        130                 135                 140

Arg Leu Met Glu Thr Ser Ser
145                 150
```

<210> SEQ ID NO 34
<211> LENGTH: 465
<212> TYPE: DNA
<213> ORGANISM: Artificial Sequence
<220> FEATURE:
<223> OTHER INFORMATION: Description of Artificial Sequence: nucleotide encoding fusion polypeptide

<400> SEQUENCE: 34

```
gacattgggc tgacacagtc tcctgcttcc ttagctgtat ctctgggca gagggccacc    60
atctcatgca gggccagcaa aagtgtcagt acatctggct ataattatat gcactggtac   120
caacagaaac aggacagcc acccaaactc ctcatctatc ttgcatccaa ctagcatct    180
ggggtccctg ccaggttcag tggcagtggg tctgggacag actttaccct caacatccat   240
cctgtggagg aggaggatgc tgcaacctat tactgtctgt atagtaggga gtttcctccg   300
tggacgttcg gtggaggcac caagctggaa ataaaacgtt ctggcggcgg cggctccatg   360
agtgttttag tgtattcttt cgcctctttc gttttaggtt ggtgccttcg tagtggcatt   420
acgtatttta cccgtttaat ggaaacttcc tcataataag ctagc                   465
```

<210> SEQ ID NO 35
<211> LENGTH: 160
<212> TYPE: PRT
<213> ORGANISM: Artificial Sequence
<220> FEATURE:
<223> OTHER INFORMATION: Description of Artificial Sequence: fusion polypeptide

<400> SEQUENCE: 35

```
Met Ala Glu Val Gln Leu Gln Gln Ser Gly Pro Glu Leu Lys Lys Pro
 1               5                  10                  15

Gly Glu Thr Val Lys Ile Ser Cys Lys Thr Ser Gly Tyr Ser Phe Thr
                20                  25                  30

Asn Tyr Gly Met Asn Trp Val Lys Gln Ala Pro Gly Lys Gly Leu Lys
            35                  40                  45

Trp Met Gly Trp Ile Asn Thr Tyr Thr Gly Glu Pro Thr Tyr Ala Asp
        50                  55                  60

Asp Phe Arg Gly Arg Phe Ala Phe Ser Leu Ala Thr Ser Ala Ser Thr
 65                  70                  75                  80

Ala Tyr Leu Gln Ile Ile Asn Leu Lys Asn Glu Asp Thr Ala Thr Tyr
                85                  90                  95
```

Phe Cys Glu Thr Tyr Asp Ser Pro Leu Gly Asp Tyr Trp Gly Gln Gly
            100                 105                 110

Thr Thr Val Thr Val Ser Ser Ser Gly Gly Gly Ser Gly Met
            115                 120                 125

Glu Gln Val Ala Asp Phe Asp Thr Ile Tyr Gln Ala Met Ile Gln Ile
        130                 135                 140

Ser Val Val Leu Cys Phe Ala Leu Gly Ile Ile Ala Gly Gly Gln Arg
145                 150                 155                 160

<210> SEQ ID NO 36
<211> LENGTH: 490
<212> TYPE: DNA
<213> ORGANISM: Artificial Sequence
<220> FEATURE:
<223> OTHER INFORMATION: Description of Artificial Sequence: nucleotide
      encoding fusion polypeptide

<400> SEQUENCE: 36

```
atggcagagg tccagcttca gcagtcagga cctgaactga agaagcctgg agagacagtc    60
aagatctcct gcaagacttc tggatattcc ttcacaaact atggaatgaa ctgggtgaag   120
caggctccag gaaagggttt aaagtggatg ggctggataa acacctacac tggagagcca   180
acatatgctg atgacttcag gggacggttt gccttctctt tggcaacctc tgccagcact   240
gcctatttgc agatcatcaa cctcaaaaat gaggacacgg ctacatattt ctgtgaaacc   300
tatgatagtc ccctcgggga ctactggggc caaggcacca cggtcaccgt ttcctcaagt   360
tctggtggtg gtggttctgg catggagcag gtcgcggatt tcgacacaat ttatcaggcg   420
atgatacaaa tctccgttgt actttgtttc gcgcttggta atcgctgg gggtcaaaga   480
taataagcta                                                          490
```

<210> SEQ ID NO 37
<211> LENGTH: 287
<212> TYPE: PRT
<213> ORGANISM: Artificial Sequence
<220> FEATURE:
<223> OTHER INFORMATION: Description of Artificial Sequence: fusion
      protein

<400> SEQUENCE: 37

Met Ala Glu Val Gln Leu Leu Glu Val Gln Leu Gln Gln Ser Gly Pro
1               5                   10                  15

Val Leu Val Lys Pro Gly Gly Ser Val Lys Met Ser Cys Lys Ala Ser
            20                  25                  30

Glu Tyr Thr Leu Thr Ser Tyr Leu Phe Gln Trp Val Lys Gln Lys Ser
        35                  40                  45

Gly Gln Gly Leu Glu Trp Ile Gly Tyr Ile Tyr Pro Tyr Asn Gly Gly
    50                  55                  60

Thr Arg Tyr Asn Glu Lys Phe Arg Gly Lys Ala Thr Leu Thr Ser Asp
65                  70                  75                  80

Lys Ser Ser Asn Thr Ala Tyr Leu Glu Leu Ser Ser Leu Thr Ser Glu
            85                  90                  95

Asp Ser Ala Val Tyr Tyr Cys Ala Arg Ser Ser Met Ser Asp Pro Gly
        100                 105                 110

Ala Asn Trp Gly Pro Gly Thr Leu Val Thr Val Ser Gly Gly Gly Gly
    115                 120                 125

Ser Gly Gly Gly Gly Ser Gly Gly Gly Ser Asp Ile Gln Met Thr
130                 135                 140

```
Gln Ser Pro Ser Ser Leu Ser Ala Ser Leu Gly Glu Arg Val Ser Leu
145                 150                 155                 160

Thr Cys Arg Ala Ser Gln Glu Ile Ser Gly Tyr Leu Tyr Trp Leu Gln
                165                 170                 175

Gln Lys Pro Asp Gly Thr Ile Lys Arg Leu Ile Tyr Ala Ala Ser Thr
            180                 185                 190

Leu Asp Ser Gly Val Pro Lys Arg Phe Ser Gly Arg Ser Gly Ser
        195                 200                 205

Asp Tyr Ser Leu Thr Ile Ser Ser Leu Glu Ser Glu Asp Phe Ala Asp
    210                 215                 220

Tyr Tyr Cys Leu Gln Tyr Ala Ser Tyr Pro Arg Thr Phe Gly Gly Gly
225                 230                 235                 240

Thr Lys Val Glu Ile Lys Arg Ala Gly Gly Gly Ser Met Ser Val
                245                 250                 255

Leu Val Tyr Ser Phe Ala Ser Phe Val Leu Gly Trp Cys Leu Arg Ser
        260                 265                 270

Gly Ile Thr Tyr Phe Thr Arg Leu Met Glu Thr Ser Ser Ala Ser
            275                 280                 285

<210> SEQ ID NO 38
<211> LENGTH: 867
<212> TYPE: DNA
<213> ORGANISM: Artificial Sequence
<220> FEATURE:
<223> OTHER INFORMATION: Description of Artificial Sequence:  nucleotide
      sequence encoding fusion protein

<400> SEQUENCE: 38
atggccgagg tgcagctgct cgaggtccag ctgcaacaat ctggacctgt gctggtaaag    60
cctgggggtt cagtgaaaat gtcctgcaag gcttctgaat acacactcac ttcttatctt   120
tttcagtggg tgaagcagaa gtcagggcag ggccttgagt ggattggata tatttatcct   180
tacaatggtg gtactcggta caatgagaag ttcagaggca aggccacact gacttcagac   240
aagtcctcca cacagccta cttggaactc agcagcctga cctctgaaga ctctgcagtc    300
tattactgtg caagatctag tatgagtgac cccggggcta actggggccc agggactctg   360
gtcactgtct ctggtggtgg tggttctggc ggcggcggct ccggtggtgg tggttctgat   420
atccaaatga cacaatctcc atcctcctta tctgcctctc tgggagaaag agtcagtctc   480
acttgtcggg caagtcagga gattagtggt tacttatact ggcttcagca gaaaccagat   540
ggaactatta aacgcctgat ctacgccgca tccactttag attctggtgt cccaaaaagg   600
ttcagtggca gtaggtctgg gtcagattat tctctcacca tcagcagcct gagtctgaa    660 gattttgcag actattactg tctacaatat gctagttatc ctcggacgtt cggtggaggc   720
accaaggttg aaatcaaacg ggctggcggc ggcggctcca tgagtgtttt agtgtattct   780
ttcgcctctt tcgttttagg ttggtgcctt cgtagtggca ttacgtattt tacccgttta   840
atggaaactt cctcataata agctagc                                       867

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence:  peptide
```

```
<400> SEQUENCE: 39

Asp Tyr Lys Asp Asp Asp Asp Lys
 1               5
```

METHODS FOR DISPLAY OF HETERODIMERIC PROTEINS ON FILAMENTOUS PHAGE USING PVII AND PIX, COMPOSITIONS, VECTORS AND COMBINATORIAL LIBRARIES

TECHNICAL FIELD

The present invention relates to cloning vectors and methods for producing a library of DNA molecules capable of expressing a fusion polypeptide on the surface of a filamentous phage particle. In particular, the invention relates to display of combinatorial libraries, particularly heterodimeric proteins, using filamentous phage pVII and pIX proteins.

BACKGROUND OF THE INVENTION

Phage display has been intensively investigated for producing combinatorial antibody libraries and for presentation of combinatorial arrays of peptide elements. See, for example, Rodi et al, *Curr. Opin. Biotechnol.*, 10:87–93, 1999; Vaughan et al, *Nat. Biotechnol.*, 16:535–539, 1998; Griffiths et al, *Curr. Opin. Biotechnol.*, 9:102–108, 1998; Zwick et al, *Curr. Opin. Biotechnol.*, 9:427–436, 1998; Dall'Acqua et al, *Curr. Opin. Struct. Biol.*, 8:443–450, 1998; Raag et al, *Faseb J.*, 9:73–80, 1995; Barbas et al, *Proc. Natl. Acad. Sci. USA*, 88:7978–7982, 1991; Kang et al, *Proc. Natl. Acad. Sci. USA*, 88:4363–4366, 1991; Huse et al, *Science*, 246:1273–1278, 1989).

However, many details of the phage particle itself have not been fully elucidated and the possibility of alternative display formats also remain to be explored. The filamentous bacteriophage fd, and similarly M13, consists of a circular, single-stranded DNA molecule surrounded by a cylinder of coat proteins (FIG. 1). The molecular mass of a particle is about $1.6 \times 10^7$ Da of which 88% is protein and 12% is DNA (Berkowitz et al, *J. Mol. Biol.*, 102:531–547, 1976). There are about 2700 molecules of the major coat protein pVIII that envelope the phage. At one end of the particle, there are five copies each of pIII and pVI that are involved in host-cell binding and in the termination of the assembly process. The other end contains five copies each of pVII and pIX that are hydrophobic peptides of 33 and 32 amino acids, respectively, required for the initiation of assembly and for maintenance of virion stability. While pIII, pVI, and pVIII have been used to display biological molecules, pVII and pIX have not been utilized (Rodi et al, *Curr. Opin. Biotechnol.*, 10:87–93, 1999; Russel et al, *J. Virol.*, 63:3284–3295, 1989).

Attempts at phage assembly in the absence of pVII and pIX almost completely abolished the production of phage. In addition, prior attempts at displaying a fusion protein on pVII or pIX previously showed that pVII and pIX were not functional with another protein fused to their N-termini (Endemann et al, *J. Mol. Biol.*, 250:496–506, 1995), indicating that display would not be feasible using pVII, pIX, or both.

Despite the enormous attention focused on pIII- and pVIII-mediated phage display, there are no descriptions of the use of pVII or pIX for display of foreign proteins, polypeptides or antigen binding molecules, such as single chain antibodies or components of a heterodimeric protein complex.

SUMMARY OF THE INVENTION

It has now been discovered that pVII and pIX can be used for displaying a peptide when fused to the N-termini of either of the two coat proteins. Of greater significance, It described herein that antibody variable regions fused to pVII and pIX engage in a dynamic interaction on the phage surface to display a functional Fv antibody, a representative heterodimeric motif. The display on phage of antibody heavy and light chain variable regions is therefore a prototype for display and assay of diverse libraries of combinatorial heterodimeric arrays in which members can function as dimeric artificial antibody species and allow for selection of novel biological activities.

Artificial antibodies are here defined as protein motifs of large diversity that use the functional strategy of the antibody molecule, but can be free of loop and framework structural constraints. When reduced to its essence, the antibody molecule is a biological device for the presentation of a combinatorial array of peptide elements in three-dimensional space. The essential feature is that while CDRs (complementarity determining regions) cooperate to form a binding site, their interaction is dynamic and functional with little structural association between the CDRs themselves. In this way, the full complement of amino acid residues are available for antigen recognition at a minimum energetic cost for binding. It is proposed that the ability to control the combinatorial design of not only sequence space, but also three-dimensional space, would recapitulate and ultimately transcend the natural design of the immune repertoire.

Thus the invention describes a combinatorial phage display format for construction of highly diverse heterodimeric polypeptide arrays.

In particular, the invention describes a filamentous phage particle encapsulating a genome encoding a fusion polypeptide, wherein the fusion polypeptide comprises an exogenous polypeptide fused to the amino terminus of a filamentous phage pVII or pIX protein. Preferably, the phage particle comprises the expressed fusion protein on the surface of the phage particle.

In a preferred embodiment, the phage genome further encodes a second fusion polypeptide, wherein the second fusion polypeptide comprises a second exogenous polypeptide fused to the amino terminus of the pIX protein and the first exogenous polypeptide in the first fusion polypeptide is fused to the amino terminus of the pVII protein. In this embodiment, the first and second fusion polypeptides can associate to form a heterodimeric protein complex, such as an immunoglobulin Fv, a catalytic Fv, a receptor, a nucleic acid binding protein or an enzyme.

In a related embodiment, the invention describes a vector for expressing a fusion protein on the surface of a filamentous phage comprising a cassette for expressing the fusion protein. The cassette includes upstream and downstream translatable DNA sequences operatively linked via a sequence of nucleotides adapted for directional ligation of an insert DNA, i.e., a polylinker, where the upstream sequence encodes a prokaryotic secretion signal, the downstream sequence encodes a pVII or pIX filamentous phage protein. The translatable DNA sequences are operatively linked to a set of DNA expression signals for expression of the translatable DNA sequences as portions of the fusion polypeptide. In a preferred variation, the vector further comprises a second cassette for expressing a second fusion protein on the surface of the filamentous phage, wherein the second cassette has the structure of the first cassette with the proviso that the first fusion protein expression cassette encodes pVII protein and the second fusion protein expression cassette encodes pIX protein. The vector is used as a phage genome to express heterodimeric protein complexes on the surface of the phage particle in which the two exogenous polypeptides of the heterodimer are anchored on the phage particle by the fusion to the first and second phage proteins, pVII and pIX, respectively.

In another embodiment, the invention contemplates a library of phage particles according to the present invention, i.e., a combinatorial library, in which representative particles in the library each display a different fusion protein. Where the particle displays a heterodimeric protein complex, the library comprises a combinatorial library of heterodimers, such as antibodies in the form of a library of Fv molecules. Preferred libraries have a diversity of at least $10^7$ different species of fusion protein.

A related embodiment describes a fusion protein comprising first and second polypeptides wherein the first polypeptide is an exogenous protein and the second polypeptide is a filamentous phage pVII or pIX protein, wherein the exogenous protein is fused to the amino terminus of the filamentous phage protein.

Still further, the invention contemplates a variety of methods for producing a combinatorial library of phage, including by cloning repertoires of genes encoding an exogenous polypeptide into a vector of the present invention, modifying the structure of the exogenous polypeptides in a library by mutagenesis, by random combination of populations of first and second fusion protein libraries, by affinity selection ("panning") to alter the diversity of a library, and the like.

The design of proteins with improved or novel functions is an important goal with a variety of medical, industrial, environmental, and basic research applications. Following the development of combinatorial antibody libraries, a powerful next step is the evolution toward artificial antibody constructs as well as other protein motifs in which dimeric species are native or might be functional.

The present invention addresses these challenges by providing a phage-display format for the construction of combinatorial heterodimeric polypeptide arrays in which pVII and pIX are utilized for the display of fusion proteins that form dimeric species. It is important to note that this is an entirely new methodology because one can independently display two protein motifs in close proximity to generate a library of functional interactions.

Inherent in the scope and power of the technology is the ability to display a variety of proteins that can engage in dimeric interactions. These include not only antibodies, but also some enzymes, hormones and hormone receptors, and DNA-binding proteins. The display technology described herein can be used for combinatorial alteration of antibody framework regions and to reorganize and miniaturize the antibody structure or to display DNA binding proteins, such as repressors, as a library of heterodimers for selection against particular DNA sequences of clinical and therapeutic importance.

Thus the present technology provides for the display and selection of mutant dimeric proteins and combinatorial libraries in which members consist of heterodimeric arrays. Using this technology, the native immunoglobulin structure, in a heterodimeric $V_H$–$V_L$ Fv format shown herein, can be modified in different ways and screened for specificity and activity. For example, by combinatorial alteration of framework regions (FRs) or other manipulations to reorganize and miniaturize the antibody structure by processes coined "complementarity determining region (CDR) shuffling" and "twinibody" formation, antibody-like secondary structures will emerge that contain new paratopes or entirely different structural elements. Selection for binding and/or catalysis against the natural antigen and/or substrate as well as some related compounds will be used to screen the libraries of heterodimeric proteins.

Furthermore, sequence randomizations to form libraries and chain-shuffling protocols to form hybrid species can lead to subsets of novel proteins. For instance, the display and modification of arrays of zinc-finger domains in homodimeric or heterodimeric form produces structures which possess specific DNA interactions. In addition, entirely new constructs are possible via the insertion of a desired encoding fragment within a preformed scaffold such as an antibody chain. Possible insertions include an enzyme signature sequence or a repressor binding protein.

It should be understood that both the foregoing general description and the following detailed description are exemplary and explanatory only and are not restrictive of the invention as claimed.

DETAILED DESCRIPTION OF THE DRAWINGS

FIG. 1 is illustrates a schematic drawing of the architecture of a filamentous phage fd, with the 10 protein-encoding genes indicated by name and location in the phage particle.

FIG. 2A illustrates the major features of the phagemid expression vector pCGMT-1b including the lacZ promoter to initiate transcription, the ribosome binding sites (RIBS) to initiate translation, the leader sequences ompA and pelB for the two polypeptides encoded in the dicistronic vector, and the relevant cloning sites. The two large blank sections indicate the stuffer fragments which are removed prior to insertion of the relevant polypeptides to be expressed.

Figure 6:
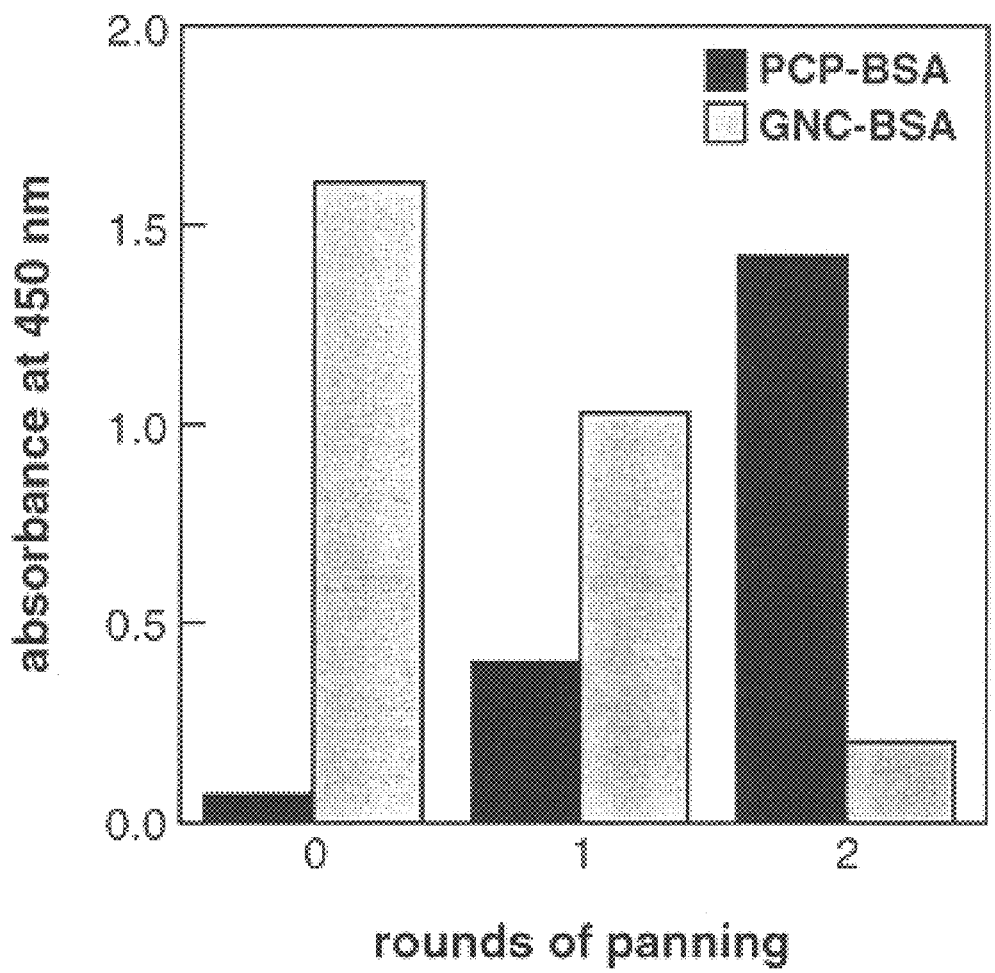

FIG. 6 illustrates the results of Phage ELISA that demonstrates the enrichment of anti-PCP 2H6 phage Fv from a mixture of 2H6 and 92H2 phage as described in the Examples. Pooled mixtures of the phage were eluted after each round of panning and were amplified; thereafter 10 billion cfu of phage were added to each well of microtiter plates precoated with PCP-BSA or GNC-BSA, and the phage ELISA was conducted to detect amount of phage particles using an anti-M13 antibody.

Figure 7A:
Figure 7B:
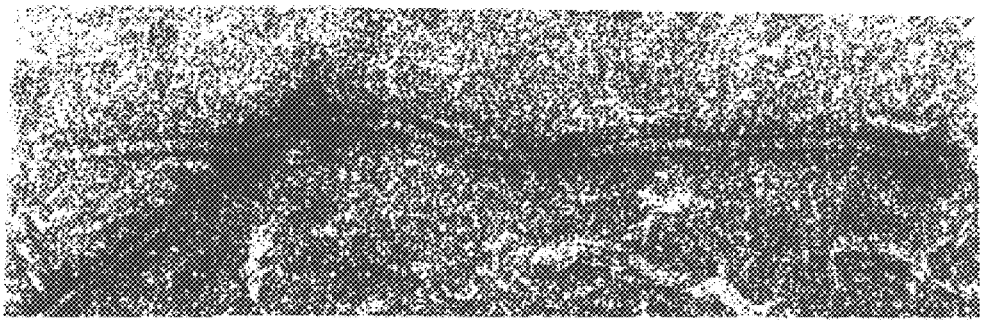

FIGS. 7A and 7B illustrates electron micrographs showing antigen specific labeling of filamentous phage displaying 2H6 Fv heterodimer as described in the Examples. FIG. 7A shows a phage specifically labeled with 5-nm colloidal gold particles adhered to the PCP-BSA antigen (x 105,000). FIG. 7B shows the phage on the same grid as in FIG. 7A but labeled with two gold particles (x 105,000).

Figure 8:
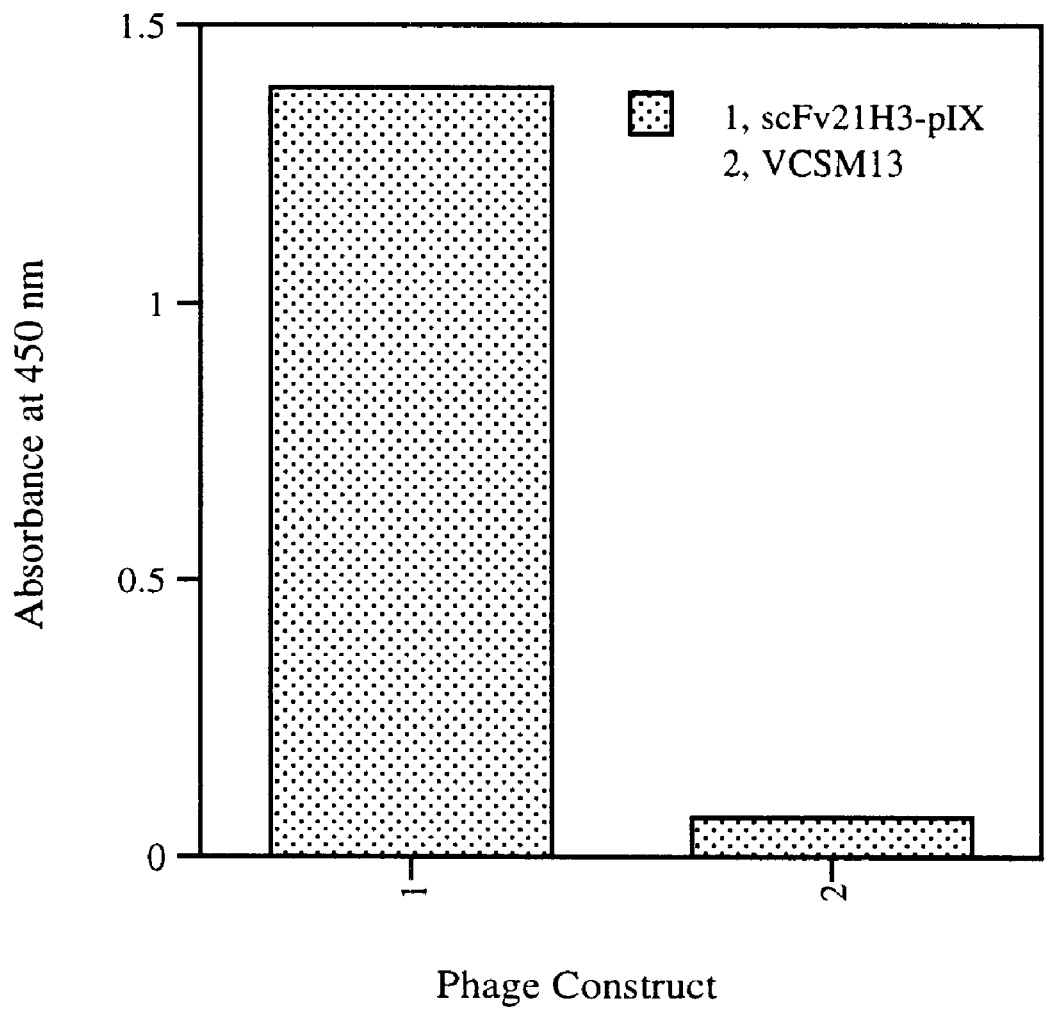

FIG. 8 illustrates the results of Phage ELISA of the single chain Fv (scFv) construct 21H3 fused to pIX (scFV21H3-pIX) using PCP-BSA antigen as described in the Examples.

DETAILED DESCRIPTION OF THE INVENTION

A. Definitions

Amino Acid Residue:

An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in J. Biol. Chem., 243:3552–59 (1969) and adopted at 37 C.F.R. 1.822 (b) (2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| J | Xaa | Unknown or other |

It should be noted that all amino acid residue sequences represented herein by formulae have a left- to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822 (b) (4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Nucleotide:

A monomeric unit of DNA or RNA consisting of a sugar moiety (pentose), a phosphate, and a nitrogenous heterocyclic base. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Nucleic Acid:

A polymer of nucleotides, either single or double stranded.

Polynucleotide:

a polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene:

A nucleic acid whose nucleotide sequence codes for an RNA or polypeptide. A gene can be either RNA or DNA.

Vector:

a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Receptor:

A receptor is a molecule, such as a protein, glycoprotein and the like, that can specifically (non-randomly) bind to another molecule.

Antibody:

The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', $F(ab')_2$ and Fv.

Antibody Combining Site:

An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Fusion Polypeptide:

A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Cistron:

Sequence of nucleotides in a DNA molecule coding for an amino acid residue sequence and including upstream and downstream DNA expression control elements.

B. Filamentous Phage

The present invention contemplates a filamentous phage comprising a matrix of proteins encapsulating a genome encoding a fusion protein (protein). The fusion protein comprises an exogenous polypeptide portion fused to the amino terminus of a filamentous phage pVII or pIX protein.

By "exogenous" is meant that the polypeptide fused to the phage protein is not normally associated with the phage pVII or pIX protein in wild-type varieties of filamentous phage, but rather are foreign to the normal phage protein.

A typical exogenous polypeptide is any polypeptide of interest, including an immunoglobulin heavy chain variable domain ($V_H$), an immunoglobulin light chain variable domain ($V_L$), natural or synthetic polypeptides, a single chain antibody (scFv), and the like.

In a preferred embodiment, a filamentous phage encapsulates a genome which encodes a first and second fusion protein, where the first fusion protein comprises a first exogenous polypeptide fused to pVII and the second fusion protein comprises a second exogenous polypeptide fused to pIX.

The filamentous phage will further contain the fusion protein(s) displayed on the surface of the phage particle, as described in the Examples. Thus, where there are first and second fusion proteins, the phage can display these proteins in a function manner such that the first and second exogenous polypeptides can interact as a heterodimer to form a functional two-chain protein complex on the phage surface.

Where an expressed heterodimeric protein has the capacity to bind ligand it is alternatively referred to herein as a ligand-binding heterodimeric receptor.

The heterodimeric receptor in a preferred embodiment is an epitope-binding complex. That is, a complex of first and second polypeptides capable of binding an epitope. Preferably, the first and second polypeptides are antibody heavy chain and light chain polypeptides. In particular, a preferred embodiment utilizes $V_H$ and $V_L$ to form an Fv complex. Other heterodimeric protein complexes include a catalytic Fv, a receptor, a nucleic acid binding protein, and enzyme and the like heterodimeric proteins.

In a fusion protein present on a phage of this invention, the "fusion" between the exogenous polypeptide and the filamentous phage pVII or pIX protein may comprise a typical amide linkage, or may comprise a linker polypeptide (i.e., a "linker") as described in the Examples. Any of a variety of linkers may be used which are typically a stretch of about 5 to 50 amino acids in length. Particularly preferred linkers provide a high degree of mobility to the fusion protein at the point of the linker. An exemplary and preferred linker has the formula $-(Gly_4Ser)_n-$, where n is 1–5. Exemplary linkers are described in the Examples.

A preferred phage contains a genome comprising the vector pCGMT or pCGMT-1b described in the Examples. A particularly preferred filamentous phage displays an Fv described in the Examples.

Because the receptor is linked to the phage in a surface accessible manner, the phage can be advantageously used as a solid-phase affinity sorbent. In preferred embodiments, the phage are linked, preferably removably linked, to a solid (aqueous insoluble) matrix such as agarose, cellulose, synthetic reins, polysaccharides and the like. For example, transformants shedding the phage can be applied to and retained in a column and maintained under conditions that support shedding of the phage. An aqueous composition containing a ligand that binds to the receptor expressed by the phage is then passed through the column at a predetermined rate and under receptor-binding conditions to form a solid-phase receptor-ligand complex. The column is then washed to remove unbound material, leaving the ligand bound to the solid-phase phage. The ligand can then be removed and recovered by washing the column with a buffer that promotes dissociation of the receptor-ligand complex.

Alternatively, purified phage can be admixed with a aqueous solution containing the ligand to be affinity purified. The receptor/ligand binding reaction admixture thus formed is maintained for a time period and under binding conditions sufficient for a phage-linked receptor-ligand complex to form. The phage-bound ligand (ligand-bearing phage) are then separated and recovered from the unbound materials, such as by centrifugation, electrophoresis, precipitation, and the like.

Phage of this invention can be labeled when used in a diagnostic method of this invention. Preferred labels include radioactively labeled nucleic acids incorporated into the phage genome, or radioactively labeled amino acids incorporated into protein components of the phage particle. Preparation of labeled phage can be routinely prepared by growing phage as described herein, but including radiolabeled nucleotides or radiolabeled amino acids in the culture medium for incorporation into nucleic acids or polypeptides of the phage, respectively. Exemplary labels are $^3$H-thymidine or $^{35}$S-methionine. Other isotopic labels and other nucleotide or amino acid precursors are readily available to one skilled in the art. The labeled phage preferably contains sufficient label to be detectable in a ligand binding assay of this invention, i.e., the phage is detectably labeled.

A filamentous phage suitable for use in the present invention can be any of a variety of phage particles, including both natural isolates of filamentous phage known in the art, modified filamentous phage, and artificial filamentous phage, so long as the basic properties necessary for practicing the present invention are preserved. Those properties comprise the capacity to encapsulate a genome which comprises an expression cassette that encodes the fusion protein, and the capacity to be formed into a particle which incorporates the pVII and pIX protein into the phage particle surface and display the exogenous polypeptide. The field of filamentous phage research and development has been extensive and therefore a large variety of filamentous phage variants have been described which would be suitable for use according to the present invention, including "phagemids", which are filamentous phage genomes adapted to behave like plasmids in addition to behaving like a filamentous phage genome.

Exemplary descriptions of the field of filamentous phage variants and phage genomes, the structure of filamentous phage particles, their coat proteins and particle assembly, see the reviews by Smith et al, "Phage Display" in *Chem.Rev.*, 97:391–410, 1997; Rached et al., *Microbiol. Rev.*, 50:401–427 (1986); and Model et al., in "The Bacteriophages: Vol. 2", R. Calendar, ed. Plenum Publishing Co., pp. 375–456, (1988).

As is noted in the field, a variety of genetic deficiencies in the wild-type filamentous phage genome can be present and complemented by the use of helper phage for production of the desired phage particle. Therefore, the invention is not to be construed to any particular phage or phagemid genome so long as the encapsulated genome can be formed in a particle with surface expressed pVII and/or pIX.

C. DNA Expression Vectors

A vector of the present invention is a recombinant DNA (rDNA) molecule adapted for receiving and expressing translatable DNA sequences in the form of a fusion polypeptide containing a filamentous phage protein selected from the group consisting of pVII and pIX protein and a prokaryotic secretion signal domain. The vector comprises a cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage pVII or pIX protein as defined herein. The cassette preferably includes DNA expression control sequences for expressing the fusion polypeptide that is produced when an insert translatable DNA sequence (insert DNA) is directionally inserted into the cassette via the sequence of nucleotides adapted for directional ligation.

An expression vector is characterized as being capable of expressing, in a compatible host, a structural gene product such as a fusion polypeptide of the present invention.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked.

As used herein with regard to DNA sequences or segments, the phrase "operatively linked" means the sequences or segments have been covalently joined, preferably by conventional phosphodiester bonds, into one strand of DNA, whether in single or double stranded form.

The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In preferred embodiments, the vector utilized includes a prokaryotic replicon i.e., a DNA sequence having the ability to direct autonomous replication and maintenance of the recombinant DNA molecule extra chromosomally in a prokaryotic host cell, such as a bacterial host cell, transformed therewith. Such replicons are well known in the art. In addition, those embodiments that include a prokaryotic replicon also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

A translatable DNA sequence is a linear series of nucleotides that provide an uninterrupted series of at least 8 codons that encode a polypeptide in one reading frame.

An upstream translatable DNA sequence encodes a prokaryotic secretion signal. The secretion signal is a leader peptide domain of protein that targets the protein to the periplasmic membrane of gram negative bacteria.

A preferred secretion signal is a pelB or ompA secretion signal. Other secretion signal polypeptide domains from *E. coli* useful in this invention include malE, ompF, phoA, Bla and lamB described in U.S. Pat. No. 5,658,727.

A downstream translatable DNA sequence encodes a filamentous pVII or pIX protein. Preferred phage proteins are obtainable from filamentous phage M13, f1, fd, and the like equivalent filamentous phage. Thus, a downstream translatable DNA sequence encodes an amino acid residue sequence that corresponds, and preferably is identical, to the filamentous phage gene VII or gene IX coat polypeptide.

Thus, the amino acid residue sequence of a preferred pVII protein is derived from the M13 filamentous phage gene VII protein (also designated pVII). A preferred pVII protein has an amino acid residue sequence shown in SEQ ID NO 21.

The amino acid residue sequence of another preferred pIX protein is derived from the M13 filamentous phage gene IX protein (also designated pIX). A preferred pIX protein has an amino acid residue sequence shown in SEQ ID NO 23.

A cassette in a DNA expression vector of this invention is the region of the vector that forms, upon insertion of a translatable DNA sequence (insert DNA), a sequence of nucleotides capable of expressing, in an appropriate host, a fusion polypeptide of this invention. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. Preferred ribosome binding sites (RIBS) are described in U.S. Pat. No. 5,658,727 and described in the Examples.

The 3' control sequences define at least one termination (stop) codon in frame with and operatively linked to the downstream translatable DNA sequence.

Thus, a DNA expression vector of this invention provides a system for cloning translatable DNA sequences into the cassette portion of the vector to produce a cistron capable of expressing a fusion polypeptide of this invention.

In preferred embodiments, a DNA expression vector provides a system for independently cloning (inserting) two translatable DNA sequences into two separate cassettes present in the vector, to form two separate cistrons for expressing both polypeptides of a heterodimeric receptor, or the ligand binding portions of the polypeptides that comprise a heterodimeric receptor. The DNA expression vector for expressing two cistrons is referred to as a dicistronic expression vector.

Thus, a preferred DNA expression vector of this invention comprises, in addition to the cassette previously described in detail, a second cassette for expressing a second fusion polypeptide. The second cassette includes upstream and downstream translatable DNA sequences as in the first cassette, which sequences are operatively linked via a sequence of nucleotides adapted for directional ligation of an insert DNA with the proviso that the upstream prokaryotic secretion signal is typically a different secretion signal from that present in the first cassette, and the downstream sequence encoding a filamentous phage protein is different from the phage protein in the first cassette. Preferably, the first fusion protein expression cassette encodes pIX protein and the second fusion protein expression cassette encodes pVII protein.

In preferred embodiments of a dicistronic expression vector, the first expression cassette includes the ompA secretion signal and the second expression cassette includes the pelB secretion signal.

The second cassette is capable, upon insertion of a translatable DNA sequence (insert DNA), of expressing the second fusion polypeptide comprising a fusion of the secretion signal with a polypeptide coded by the insert DNA.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication. See, for example, Rasched et al., *Microbiol. Rev.*, 50:401–427 (1986); and Horiuchi, *J. Mol. Biol.*, 188:215–223 (1986).

A preferred filamentous phage origin of replication for use in the present invention is a M13, f1 or fd phage origin of replication. Preferred DNA expression vectors of this invention are the vector pCGMT and the dicistronic expression vector pCGMT-1b described in Example 1.

A preferred vector can be produced using a variety of means well known in the recombinant DNA arts, and therefore the invention should not be so limited. A preferred method for preparing the exemplary vectors of this invention comprises preparing overlapping synthetic oligonucleotides based on the complete nucleotide sequence, and ligation of the synthetic oligonucleotides to form a complete sequence, using well known design, synthesis and ligation methods.

Insofar as a vector of this invention may be manipulated to contain an insert DNA, thereby having the capacity to express a fusion polypeptide, one embodiment contemplates the previously described vectors containing an insert DNA. Particularly preferred vectors containing antibody genes are described in the Examples.

D. Fusion Polypeptides

In another embodiment, the present invention contemplates a fusion polypeptide (protein) comprising first and second polypeptides operatively linked (fused). The first polypeptide is an exogenous protein and the second polypeptide is a filamentous phage pVII or pIX protein, whereby the exogenous protein is fused to the amino terminus of the filamentous phage protein.

Where the fusion protein is in the immature form, i.e., where the leader sequence has not been processed (removed), a fusion protein can also contain a amino terminal prokaryotic secretion signal, such as pelB, ompA and the like as described herein.

In a preferred embodiment, the exogenous polypeptide is an immunoglobulin heavy chain variable domain ($V_H$), an immunoglobulin light chain variable domain ($V_L$) , natural or synthetic polypeptides, a single chain antibody (scFv), and the like.

As used herein with regard to polypeptides, the phrase "operatively linked" means that polypeptide fragments, or protein domains represented by polypeptides, have been covalently joined into a single polypeptide polymer, typically by conventional amide bonds between the adjacent amino acids being linked in the polypeptide. The term also implicates a more extensive connection by means of a linker polypeptide as described in more detail herein above. A preferred fusion polypeptide has a linker according to the formula $(Gly_4Ser)_n$, where n is from 1 to 5.

E. Methods for Producing a Library

1. General Rationale

In one embodiment the present invention provides a system for the simultaneous cloning and screening of preselected ligand-binding specificities from gene repertoires using a single vector system. This system provides linkage of cloning and screening methodologies and has two requirements. First, that expression of the polypeptide chains of a heterodimeric receptor in an in vitro expression host such as *E. coli* requires coexpression of the two polypeptide chains in order that a functional heterodimeric receptor can assemble on the phage surface to produce a receptor that binds ligand. Second, that screening of isolated members of the library for a preselected ligand-binding capacity requires a means to correlate (a linkage) the binding capacity of an expressed receptor molecule with a convenient means to isolate the gene that encodes the member from the library.

Linkage of expression and screening is accomplished by the combination of targeting of a fusion polypeptide into the periplasm of a bacterial cell to allow processing and assembly of a functional fusion protein, and the targeting of a fusion polypeptide onto the coat of a filamentous phage particle during phage assembly to allow for convenient screening of the library member of interest. Periplasmic targeting is provided by the presence of a secretion signal domain in a fusion polypeptide of this invention. Targeting to a phage particle surface is provided by the presence of a filamentous phage pVII or pIX protein in a fusion polypeptide of this invention.

The present invention describes in one embodiment a method for producing a library of DNA molecules, each DNA molecule comprising a cistron for expressing a fusion polypeptide on the surface of a filamentous phage particle. The method comprises the steps of (a) forming a ligation admixture by combining in a ligation buffer (I) a repertoire of polypeptide encoding genes and (ii) a plurality of DNA expression vectors in linear form adapted to form a fusion polypeptide expressing cistron, and (b) subjecting the admixture to ligation conditions for a time period sufficient for the repertoire of genes to become operatively linked (ligated) to the plurality of vectors to form the library.

In this embodiment, the repertoire of polypeptide encoding genes are in the form of double-stranded (ds) DNA and each member of the repertoire has cohesive termini adapted for directional ligation. In addition, the plurality of DNA expression vectors are each linear DNA molecules having upstream and downstream cohesive termini that are (a) adapted for directionally receiving the polypeptide genes in a common reading frame, and (b) operatively linked to respective upstream and downstream translatable DNA sequences. The upstream translatable DNA sequence encodes a secretion signal, preferably a pelB or ompA secretion signal, and the downstream translatable DNA sequence encodes a filamentous phage pVII or pIX protein as described herein for a fusion polypeptide of this invention. The translatable DNA sequences are also operatively linked to respective upstream and downstream DNA expression control sequences as defined for a DNA expression vector described herein.

The library so produced can be utilized for expression and screening of the fusion polypeptides encoded by the resulting library of cistrons represented in the library by the expression and screening methods described herein.

2. Production of Gene Repertoires

A gene repertoire is a collection of different genes, preferably polypeptide-encoding genes (polypeptide genes), and may be isolated from natural sources or can be generated artificially. Preferred gene repertoires are comprised of conserved genes. Particularly preferred gene repertoires comprise either or both genes that code for the members of a dimeric receptor molecule.

A gene repertoire useful in practicing the present invention contains at least $10^3$, preferably at least $10^4$, more preferably at least $10^5$, and most preferably at least $10^7$ different genes, although higher diversity amount of $10^9$ and even $10^{11}$ are possible because of the library properties inherent when propagating filamentous phage. Methods for evaluating the diversity of a repertoire of genes is well known to one skilled in the art.

Thus, in one embodiment, the present invention contemplates a method of isolating a pair of genes coding for a dimeric protein complex having a preselected activity from a repertoire of conserved genes. Additionally, expressing the cloned pair of genes and isolating the resulting expressed dimeric protein complex is also described. Preferably, the protein complex will be a heterodimeric polypeptide capable of binding a ligand, such as an antibody molecule or immunologically active portion thereof, a cellular receptor, or a cellular adhesion protein coded for by one of the members of a family of conserved genes, i.e., genes containing a conserved nucleotide sequence of at least about 10 nucleotides in length. As shown herein, the protein complex can also be a catalytic antibody.

Exemplary conserved gene families encoding different polypeptide chains of a dimeric receptor are those coding for immunoglobulins, major histocompatibility complex antigens of class I or II, lymphocyte receptors, integrins and the like.

A gene can be identified as belonging to a repertoire of conserved genes using several methods. For example, an isolated gene may be used as a hybridization probe under low stringency conditions to detect other members of the repertoire of conserved genes present in genomic DNA using the methods described by Southern, *J. Mol. Biol.*, 98:503 (1975). If the gene used as a hybridization probe hybridizes to multiple restriction endonuclease fragments of the genome, that gene is a member of a repertoire of conserved genes.

The immunoglobulins, or antibody molecules, are a large family of molecules that include several types of molecules, such as IgD, IgG, IgA, IgM and IgE. The antibody molecule is typically comprised of two heavy (H) and light (L) chains with both a variable (V) and constant © region present on each chain. Several different regions of an immunoglobulin contain conserved sequences useful for isolating an immunoglobulin repertoire. Extensive amino acid and nucleic acid sequence data displaying exemplary conserved sequences is compiled for immunoglobulin molecules by Kabat et al., in *Sequences of Proteins of Immunological Interest*, National Institutes of Health, Bethesda, Md., 1987.

The major histocompatibility complex (MHC) is a large genetic locus that encodes an extensive family of proteins that include several classes of molecules referred to as class I, class II or class III MHC molecules. Paul et al., in *Fundamental Immunology*, Raven Press, N.Y., pp. 303–378 (1984).

Lymphocytes contain several families of proteins on their cell surfaces including the T-cell receptor, Thy-1 antigen and numerous T-cell surface antigens including the antigens defined by the monoclonal antibodies OKT4 (leu3), OKT5/8 (leu2), OKT3, OKT1 (leu1), OKT 11 (leu5) OKT6 and OKT9. Paul, supra at pp. 458–479.

Adhesive proteins involved in cell attachment are members of a large family of related proteins termed integrins. Integrins are heterodimers comprised of a beta and an alpha subunit. Members of the integrin family include the cell surface glycoproteins platelet receptor GpIIb-IIIa, vitronectin receptor (VnR), fibronectin receptor (FnR) and the leukocyte adhesion receptors LFA-1, Mac-1, Mo-1 and 60.3. Rouslahti et al., *Science*, 238:491–497 (1987). Nucleic acid and protein sequence data demonstrates regions of conserved sequences exist in the members of these families, particularly between the beta chain of GpIIb-IIIa, VnR and FnR, and between the alpha subunit of VnR, Mac-1, LFA-1, FnR and GpIIb-IIIa. Suzuki et al., *Proc. Natl. Acad. Sci. USA*, 83:8614–8618, 1986; Ginsberg et al., *J. Biol. Chem.*, 262:5437–5440, 1987.

Various well known methods can be employed to produce a useful gene repertoire. For instance, $V_H$ and $V_L$ gene repertoires can be produced by isolating $V_H$- and $V_L$-coding mRNA from a heterogeneous population of antibody producing cells, i.e., B lymphocytes (B cells), preferably rearranged B cells such as those found in the circulation or spleen of a vertebrate. Rearranged B cells are those in which immunoglobulin gene translocation, i.e., rearrangement, has occurred as evidenced by the presence in the cell of mRNA with the immunoglobulin gene V, D and J region transcripts adjacently located thereon. Typically, the B cells are collected in a 1–100 ml sample of blood which usually contains $10^6$ B cells/ml.

In some cases, it is desirable to bias a repertoire for a preselected activity, such as by using as a source of nucleic acid cells (source cells) from vertebrates in any one of various stages of age, health and immune response. For example, repeated immunization of a healthy animal prior to collecting rearranged B cells results in obtaining a repertoire enriched for genetic material producing a receptor of high affinity. Mullinax et al., *Proc. Natl. Acad. Sci. USA*, 87:8095–8099 (1990). Conversely, collecting rearranged B cells from a healthy animal whose immune system has not been recently challenged (i.e., a naive immune system) results in producing a repertoire that is not biased towards the production of high affinity $V_H$ and/or $V_L$ polypeptides.

Methods for preparing fragments of genomic DNA from which immunoglobulin variable region genes can be cloned as a diverse population are well known in the art. See for example U.S. Pat. No. 5,658,727, Herrmann et al., *Methods In Enzymol.*, 152:180–183, (1987); Frischauf, *Methods In Enzymol.*, 152:183–190 (1987); Frischauf, *Methods In Enzymol.*, 152:190–199 (1987); and DiLella et al., *Methods In Enzymol.*, 152:199–212 (1987). (The teachings of the references cited herein are hereby incorporated by reference.)

The desired gene repertoire can be isolated from either genomic material containing the gene expressing the variable region or the messenger RNA (mRNA) which represents a transcript of the variable region.

3. Preparation of Polynucleotide Primers

The term "polynucleotide" as used herein in reference to primers, probes and nucleic acid fragments or segments to be synthesized by primer extension is defined as a molecule comprised of two or more deoxyribonucleotide or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on may factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

The polynucleotide primers can be prepared using any suitable method, such as, for example, the phosphotriester or phosphodiester methods see Narang et al., *Meth. Enzymol.*, 68:90, (1979); U.S. Pat. No. 4,356,270; and Brown et al., *Meth. Enzymol.*, 68:109, (1979).

The choice of a primer's nucleotide sequence depends on factors such as the distance on the nucleic acid from the region coding for the desired receptor, its hybridization site on the nucleic acid relative to any second primer to be used, the number of genes in the repertoire it is to hybridize to, and the like.

a. Primers for Producing Immunoglobulin Gene Repertoires $V_H$ and $V_L$ gene repertoires can be separately prepared prior to their utilization in the present invention. Repertoire preparation is typically accomplished by primer extension, preferably by primer extension in a polymerase chain reaction (PCR) format.

If the repertoires of $V_H$-coding and $V_L$-coding DNA homologs are to be produced by (PCR) amplification, two primers, i.e., a PCR primer pair, must be used for each coding strand of nucleic acid to be amplified. The first primer becomes part of the nonsense (minus or complementary) strand and hybridizes to a nucleotide sequence conserved among $V_H$ (plus or coding) strands within the repertoire. To produce $V_H$ coding DNA homologs, first primers are therefore chosen to hybridize to (i.e. be complementary to) conserved regions within the J region, CH1 region, hinge region, CH2 region, or CH3 region of immunoglobulin genes and the like. To produce a $V_L$ coding DNA homolog, first primers are chosen to hybridize with (i.e. be complementary to) a conserved region within the J region or constant region of immunoglobulin light chain genes and the like. Second primers become part of the coding (plus) strand and hybridize to a nucleotide sequence conserved among minus strands. To produce the $V_H$-coding DNA homologs, second primers are therefore chosen to hybridize with a conserved nucleotide sequence at the 5' end of the $V_H$-coding immunoglobulin gene such as in that area coding for the leader or first framework region. It should be noted that in the amplification of both $V_H$- and $V_L$-coding DNA homologs the conserved 5' nucleotide sequence of the second primer can be complementary to a sequence exogenously added using terminal deoxynucleotidyl transferase as described by Loh et al., *Science*, 243:217–220 (1989). One or both of the first and second primers can contain a nucleotide sequence defining an endonuclease recognition site. The site can be heterologous to the immunoglobulin gene being amplified and typically appears at or near the 5' end of the primer.

When present, the restriction site-defining portion is typically located in a 5'-terminal non-priming portion of the primer. The restriction site defined by the first primer is typically chosen to be one recognized by a restriction enzyme that does not recognize the restriction site defined by the second primer, the objective being to be able to produce a DNA molecule having cohesive termini that are non-complementary to each other and thus allow directional insertion into a vector.

4. Polymerase Chain Reaction to Produce Gene Repertoires

The strategy used for cloning the $V_H$ and $V_L$ genes contained within a repertoire will depend, as is well known in the art, on the type, complexity, and purity of the nucleic acids making up the repertoire. Other factors include whether or not the genes are contained in one or a plurality of repertoires and whether or not they are to be amplified and/or mutagenized.

After producing $V_H$- and $V_L$-coding DNA homologs for a plurality of different $V_H$- and $V_L$-coding genes within the repertoires, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector.

PCR amplification methods are described in detail in U.S. Pat. Nos. 4,683,195, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

5. Linear DNA Expression Vectors

A DNA expression vector for use in a method of the invention for producing a library of DNA molecules is a linearized DNA molecule as described before having two (upstream and downstream) cohesive termini adapted for directional ligation to a polypeptide gene.

A linear DNA expression vector is typically prepared by restriction endonuclease digestion of a circular DNA expression vector of this invention to cut at two preselected restriction sites within the sequence of nucleotides of the vector adapted for directional ligation to produce a linear DNA molecule having the required cohesive termini that are adapted for direction ligation. Directional ligation refers to the presence of two (a first and second) cohesive termini on a vector, or on the insert DNA molecule to be ligated into the vector selected, so that the termini on a single molecule are not complementary. A first terminus of the vector is complementary to a first terminus of the insert, and the second terminus of the vector is complementary to the second terminus of the insert.

In preparing a library of DNA molecules of this invention, a ligation admixture is prepared as described above, and the admixture is subjected to ligation conditions for a time period sufficient for the admixed repertoire of polypeptide genes to ligate (become operatively linked) to the plurality of DNA expression vectors to form the library.

Ligation conditions are conditions selected to favor a ligation reaction wherein a phosphodiester bond is formed between adjacent 3' hydroxyl and 5' phosphoryl termini of DNA. The ligation reaction is preferably catalyzed by the enzyme T4 DNA ligase. Ligation conditions can vary in time, temperature, concentration of buffers, quantities of DNA molecules to be ligated, and amounts of ligase, as is well known.

6. Preparation of Dicistronic Gene Libraries

In a particularly preferred embodiment, the present invention contemplates methods for the preparation of a library of dicistronic DNA molecules. A dicistronic DNA molecule is a single DNA molecule having the capacity to express two separate polypeptides from two separate cistrons. In preferred embodiments, the two cistrons are operatively linked at relative locations on the DNA molecule such that both cistrons are under the transcriptional control of a single promoter. Each dicistronic molecule is capable of expressing first and second polypeptides from first and second cistrons, respectively, that can form, in a suitable host, a heterodimeric receptor on the surface of a filamentous phage particle.

Preferred methods for producing a library of dicistronic DNA molecules are described in more detail in the Examples.

DNA expression vectors useful for practicing the above method are the dicistronic expression vectors described in greater detail herein.

In practicing the method of producing a library of dicistronic DNA molecules, the dicistronic vectors contain different sets of cohesive termini for cloning (inserting) the first and second insert DNA molecules, referred to as upstream and downstream first cohesive termini, and upstream and downstream second cohesive termini, respectively. In this embodiment, the treating step to linearize the circular DNA molecules typically involves the use of restriction endonucleases that are specific for producing said second termini, but do not cleave the circular DNA molecule at the sites that formed the first termini. Exemplary and preferred first and second termini are the termini defined by cleavage of pCGMT-1b with Sac I and Xba I to form the upstream and downstream first termini, and defined by cleavage of pCGMT-1b with Nco I and Nhe I to form the upstream and downstream second termini. In this embodiment, other pairs of cohesive termini can be utilized at the respective pairs of first and second termini, so long as the four termini are each distinct, non-complementary termini.

Methods of treating the plurality of circular DNA molecules under DNA cleavage conditions to form linear DNA molecules are generally well known and depend on the nucleotide sequence to be cleaved and the mechanism for cleavage. Preferred treatments involve admixing the DNA molecules with a restriction endonuclease specific for a endonuclease recognition site at the desired cleavage location in an amount sufficient for the restriction endonuclease to cleave the DNA molecule. Buffers, cleavage conditions, and substrate concentrations for restriction endonuclease cleavage are well known and depend on the particular enzyme utilized.

7. Methods for Changing the Diversity of a Library

The present invention provides methods for changing the diversity of a library of filamentous phage library of this invention. These methods generally increase the diversity of the library, thereby increasing the pool of possible epitope-binding complexes from which to screen for a desired binding activity. Alternatively, the methods can be directed at enriching for a class of epitope-binding complexes. The class is typically defined by the ability to bind a particular epitope or family of epitopes present on a preselected antigen or group of antigens. Alternatively, where catalysis is the desired activity, the class can be a catalytic activity.

a. Increasing Library Diversity by Mutation

A particularly preferred method for increasing diversity is to alter the amino acid residue sequence of one or more polypeptides of the epitope-binding complex encoded by the genome of a phage of this invention. Alterations can be conveniently introduced at the nucleic acid level by mutation of the nucleic acid. The method can be practiced on a single species of nucleic acid coding a polypeptide of this invention, or can be practiced on a library of nucleic acids present in a library of phage of this invention.

Mutation of nucleic acid can be conducted by a variety of means well known in the art, and in particular as described in U.S. Pat. No. 5,658,727.

Thus, the invention contemplates a method for increasing the diversity of a library of filamentous phage particles comprising the steps of: a) providing a library of filamentous phage particles according to the present invention, and b) mutating the nucleotide sequence encoding the exogenous polypeptide in its functional site, such as in the immunoglobulin variable domain-coding nucleotide sequence, present in each DNA expression vector in the library to form a library of phage particles each containing, for example, a mutated immunoglobulin variable domain nucleotide sequence.

The providing can include manipulating the genomes of the phage particles in the library in order to isolate the nucleic acids in preparation for a mutagenizing PCR reaction. Manipulations of a phage library to isolate the phage genome for use in a PCR reaction is described elsewhere herein.

In one embodiment, the mutating comprises subjecting the immunoglobulin variable domain-coding nucleotide sequence to an error-prone polymerase chain reaction. In another embodiment, the mutating comprises subjecting the immunoglobulin variable domain-coding nucleotide sequence to a method for mutating a CDR of the immunoglobulin variable domain-coding nucleotide sequence using a CDR-directed oligonucleotide as described in U.S. Pat. No. 5,658,727.

b. Enrichment of a Library

The invention describes a method to change the diversity of the library by enriching the library for a preselected class of epitope-binding complexes. The process generally involves affinity selection of those phage particles in a library that are capable of binding a preselected antigen. The process of affinity selection, or panning, is described in detail in the Examples.

Thus the invention contemplates a method for changing the diversity of a library of filamentous phage particles comprising the steps of a) providing a library of filamentous phage particles according to the present invention, b) contacting the provided library with a preselected ligand under conditions sufficient for members of the library to bind to the ligand and form a ligand-phage particle complex, and c) isolating phage particles in the complex away from non-bound library members to form a ligand-enriched library comprising phage particles having binding specificity for the preselected ligand.

In preferred embodiments, the preselected ligand is affixed to a solid support, and the ligand-phage particle complex is formed in the solid phase. This embodiment further comprises the steps of i) washing the solid support after the contacting step to rinse non-bound library members from the solid support; and ii) eluting any solid-phase bound phage particles off of the solid support. The eluted phage particles are collected, thereby forming isolated phage particles that comprise an enriched library.

Elution can be conducted under a variety of conditions that disrupt the ligand-epitope-binding complex interaction. Typical conditions include high salt or low pH buffers. Particularly preferred are buffers of about pH 1 to 5, preferably about pH 2 to 3. Alternatively, the interaction can be disrupted by competition with an excess amount of the preselected ligand in the elution buffer. Both elution procedures are described in the Examples.

A related embodiment combines the features of both increasing diversity of a library by mutation and enriching the library by panning to "mature" epitope-binding complex affinities for a preselected ligand. Thus it is possible to evolve new binding specificities, and more potent binding specificities, using the present methods for changing library diversity.

The combination of these methods can be configured in a variety of ways, as will be apparent to a skilled practitioner. For example, one can isolate a library, mutagenize (diversify), and then screen (enrich) for a particular binding activity. Alternatively, one can enrich for a particular activity from a library, mutagenize the specific epitope-binding complex and further enrich the library produced by the mutagenesis.

F. Phage Libraries

The present invention contemplates a library of DNA molecules that each encode a fusion polypeptide of this invention where the library is in the form of a population of different filamentous phage particles each containing a different rDNA molecule of this invention. By different rDNA molecule is meant a rDNA molecule differing in nucleotide base sequence encoding a polypeptide of this invention when compared in nucleotide sequence to another rDNA molecule in the library.

Thus, a phage library is a population of filamentous phage, preferably f1, fd or M13 filamentous phage, each phage having packaged inside the particle a rDNA expression vector of this invention, the rDNA is encapsulated in the phage particle by the matrix proteins of the phage. Stated differently, a phage library contains a plurality of filamentous phage particles, each different phage particle containing at least one fusion protein complex on its surface as described herein. A preferred library is comprised of phage particles containing DNA molecules that encode at least $10^6$, preferably $10^7$ and more preferably $10^{8-9}$ different fusion polypeptides of this invention. By different fusion polypeptides is meant fusion polypeptides differing in amino acid residue sequence. Even higher library diversities are available when the methods of random combination or mutagenesis are utilized as described herein to increase library diversity.

Where the packaged expression vector encodes first and second polypeptides of an autogenously assembling receptor, e.g. $V_H$ and $V_L$ polypeptides that form a Fab, the library can also be characterized as containing or expressing a multiplicity of receptor specificities. Thus, libraries express at least $10^5$, preferably at least $10^6$ and more preferably at least $10^7$ different receptors, such as different antibodies, T cell receptors, integrins and the like.

The size of the library can vary depending on a number of factors, particularly the method in which the library is produced. As used herein, size connotes the complexity or diversity of the library, that is the number of different species making up the library, rather than the absolute number of particles in the library.

Thus, where a library is produced by first separately cloning two repertoires of genes, corresponding to the first and second polypeptides, the resulting library size after randomly combining the two repertoires in the form of a dicistronic vector is greatly increased. For example, consider light chain and heavy chain variable antibody gene repertoires, each having $10^6$ different members. Combining the two repertoires theoretically yields a library of $10^{12}$ possible different dicistronic vector species.

Library complexity can also be increased using the methods herein for mutating nucleotide sequences in a pre-existing library of sequences. Stated in terms of amino acid residue differences for an expressed fusion polypeptide, there can be potentially a twenty-fold increase in library size for each amino acid residue position that is targeted for random mutation.

For example, using the complementarity determining region (CDR)-directed mutagenesis of antibody genes as described in U.S. Pat. No. 5,658,727, a linear region of, for example, 16 amino acid residues can be targeted for random mutation. Starting with a single species and mutating all 16 residue positions through all possible combinations with a choice of 20 different amino acids would theoretically produce a library of $20^{16}$ different species, or $6 \times 10^{20}$ different species.

As described herein, a particular advantage of a filamentous phage in the present invention is that the DNA molecule present in the phage particle and encoding one or both of the members of the heterodimeric receptor can be segregated from other DNA molecules present in the library on the basis of the presence of the particular expressed fusion polypeptide the surface of the phage particle.

Isolation (segregation) of a DNA molecule encoding one or both members of a heterodimeric receptor is conducted by segregation of the filamentous phage particle containing the gene or genes of interest away from the population of other phage particles comprising the library. Segregation of phage particles involves the physical separation and propagation of individual phage particles away from other particles in the library. Methods for physical separation of filamentous phage particles to produce individual particles, and the propagation of the individual particles to form populations of progeny phage derived from the individual segregated particle are well known in the filamentous phage arts.

A preferred separation method involves the identification of the expressed heterodimer on the surface of the phage particle by means of a ligand binding specificity between the phage particle and a preselected ligand. Exemplary and preferred is the use of "panning" methods whereby a suspension of phage particles is contacted with a solid phase ligand (antigen) and allowed to specifically bind (or immunoreact where the heterodimer includes an immunoglobulin variable domain). After binding, non-bound particles are washed off the solid phase, and the bound phage particles are those that contain ligand-specific heterodimeric receptor (heterodimer) on their surface. The bound particles can then be recovered by elution of the bound particle from the solid phase, typically by the use of aqueous solvents that interfere with the ligand-receptor interaction. Typical solvent include buffers having high ionic strength, low pH, or an amount of soluble competing ligand sufficient to disrupt the receptor-ligand binding interaction.

An alternate method for separating a phage particle based on the ligand specificity of the surface-expressed heterodimer from a population of particles is to precipitate the phage particles from the solution phase by crosslinkage with the ligand.

The use of the above particle segregation methods provides a means for screening a population of filamentous phage particles present in a phage library of this invention. As applied to a phage library, screening can be utilized to enrich the library for one or more particles that express a heterodimer having a preselected ligand binding specificity. Where the library is designed to contain multiple species of heterodimers that all have some detectable measure of ligand binding activity, but differ in protein structure, antigenicity, ligand binding affinity or avidity, and the like, the screening methods can be utilized sequentially to first produce a library enriched for a preselected binding specificity, and then to produce a second library further enriched by further screening comprising one or more isolated phage particles. Methods for measuring ligand binding activities, antigenicity and the like interactions between a ligand and a receptor are generally well known and are not discussed further as they are not essential features of the present invention.

Thus, in one embodiment, a phage library is a population of particles enriched for a preselected ligand binding specificity.

In another embodiment, a phage library comprises a population of particles wherein each particle contains at least one fusion polypeptide of this invention on the surface of the phage particle. In a preferred embodiment, a phage library comprises a heterodimeric protein complex involving a first and second fusion protein as described herein and attached to the phage particle by pVII and pIX, respectively. Such a phage particle in this library further contains a dicistronic expression vector genome for expression of the first and second fusion proteins.

A filamentous phage particle in a library of this invention is produced by standard filamentous phage particle preparation methods and depends on the presence in a DNA expression vector of this invention of a filamentous phage origin of replication as described herein to provide the signals necessary for (1) production of a single-stranded filamentous phage replicative form and (2) packaging of the replicative form into a filamentous phage particle. Such a DNA molecule can be packaged when present in a bacterial cell host upon introduction of genetic complementation to provide the filamentous phage proteins required for production of infectious phage particles. A typical and preferred method for genetic complementation is to infect a bacterial host cell containing a DNA expression vector of this invention with a helper filamentous phage such as wild-type phage, e.g., M13, although modified phage are preferred, such as VCSM13 described herein, thereby providing the genetic elements required for phage particle assembly. Exemplary helper rescue methods are described herein.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

Examples

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Construction of Vectors for Expression of $V_H$ and $V_L$ Heterodimeric Fusion Proteins a. Primers for Polymerase Chain Reactions (PCR)

In order to prepare the various constructs described herein, oligonucleotide primers are prepared using standard oligonucleotide synthesizers to produce primers suitable for conducting polymerase chain reactions (PCR), as is well known.

For the construction of Flag and pVII/pIX fusion proteins, a Flag peptide (Asp-Tyr-Lys-Asp-Asp-Asp-Asp-Lys) (SEQ ID NO39) was fused to either the N or C-terminus of pVII and pIX. The constructs were amplified by PCR with single-stranded VCSM13 DNA as template. The primers used for the four permutations were as follows: to produce pVII-Flag: VII-FOR: (5'-CTATCCATGGCAATGGAGCAGGTCGCGGATTTC-3') (SEQ ID NO 1) and VII-fBW: (5'-ATTTAGCTAGCTTATTTGTCATCGT-CATCTTTGTAGTCT CTTTGACCCCCAGCGATTAT-3') (SEQ ID NO 2); to produce Flag-pVII: VII-fFOR (5'-CTATCCATGGCAGACTACAAAGATGAC-GATGACAAAATGG AGCAGGTCGCGGATTTC-3') (SEQ ID NO 3) and VII-BW (5'-GATTTAGC TAGCTTATTATCTTTGACCCCCAGCGATTAT-3') (SEQ ID NO 4); to produce pIX-Flag: IX-FOR (5'- CTATCCATG-GCAATGAGTGTTTTAGTGTA TTCT-3') (SEQ ID NO 5) and IX-fBW (5'-ATTTAGCTAGCTTATTTGTCA TCGT-CATCTTTGTAGTCTGAGGAAGTTTCCATTAA ACG-3') (SEQ ID NO 6); to produce Flag-pIX: IX-fFOR (5'-

CTATCCATGGCAGACTACAAAGATGA
CGATGACAAAATGAGTGTTTTAGTGTATTCT-3')
(SEQ ID NO 7) and IX-BW (5'-
GATTAGCTAGCTTATTATGAGGAAGTTTCCATTAA
ACG-3') (SEQ ID NO 8).

The PCR products resulting from the PCR reactions using VCSM13 and the above primer pairs were digested by restriction enzymes, Nco I and Nhe I, and inserted into the phagemid vector pCGMT (Gao et al, *Proc. Natl. Acad. Sci. USA*, 94:11777–11782, 1997), to form four Flag fusion protein constructs: pVII-Flag, Flag-pVII, pIX-Flag and Flag-pIX. The complete nucleotide sequence for vector pCGMT is shown in SEQ ID NO 19.

To prepare antibody variable (V) region chain fusion proteins that contain either a M13 pVII or M13 pIX protein, the following primers were used:

H1 (5'-GCCTACGGCAGCCGCTGGATTGTTATTACT-3') (SEQ ID NO 9); H2 (5'-GCCAGAACCACCACCAGAGACAGTGACCAG-3') (SEQ ID NO 10); H3 (5'-GCCAGAACCACCACCAGAGACGGTGACTGAG GTTCC-3') (SEQ ID NO 11); H4 (5'-GCCAGAACCACCACCAGATGAGGAAACG-GTGA CCGT-3') (SEQ ID NO 12); L1 (5'-GCTATCGCGATTGCTGTGGCACTGGCTGGT-3') (SEQ ID NO 13); L2 (5'-GGAGCCGCCGCCGCCAGAATCAGCCCGTTTGA TTTC-3') (SEQ ID NO 14); L3 (5'-GGAGCCGCCGCCGCCAGAATCAGTC-CGTTTCAACTC -3') (SEQ ID NO 15); L4 (5'-GGAGCCGCCGCCGCCAGAGACCAGGCCCCCG AGGCC-3') (SEQ ID NO 16); VIIF (5'-TCTGGTGGTGGTTCTGGCATGGAG CAGGTCGCGATTTC-3') (SEQ ID NO 17); IXF (5'-TCTGGCGGCGGCGGCT CCATGAGTGTTTTAGTGTATTCT-3') (SEQ ID NO 18).

b. Construction of Antibody Variable Region pVII or pIX Fusion proteins

In order to prepare the constructs designated $V_H$-(Gly$_4$Ser)-pVII and $V_L$-(Gly$_4$Ser)-pIX, V chains from two different murine catalytic antibodies, 21H3 and 2H6 (Gao et al, *Proc. Natl. Acad. Sci. USA*, 94:11777–11782, 1997; Janda et al, *Science*, 244:437–440, 1989; Lo et al, *Isr. J. Chem.*, 36:195–198, 1996; Wirsching et al, *Science*, 252:680–685, 1991), and one murine anti-cocaine antibody, 92H2 (generated by our laboratory), were used such that genes encoding the heavy chain variable domain polypeptide ($V_H$) or light chain variable domain polypeptide ($V_L$) were provided from the cloned monoclonal antibodies to construct fusion genes for expressing the $V_H$-(Gly$_4$Ser)-pVII and $V_L$-(Gly$_4$Ser)-pIX fusion proteins.

In this example, the $V_H$ sequences in each case were fused to the N-terminus of pVII, and the $V_L$ sequences were fused to the N-terminus of pIX. The constructs were engineered by inserting a linker sequence, Gly$_4$Ser, (SEQ ID NO 37, from 249–253) between $V_H$ and pVII, and between $V_L$ and pIX. The Fab genes for 21H3, 2H6 and 92H2 were available from previous work cited above and were the most readily manipulated sequences for amplification of variable regions. First, the $V_H$-linker fragments were amplified by PCR using primers H1 and H2 for Fab 21H3, H1 and H3 for Fab 2H6, and H1 and H4 for Fab 92H2. The $V_L$-linker fragments were amplified using primers L1 and L2 for Fab 21H3, L1 and L3 for Fab 2H6, and L1 and L4 for Fab 92H2. Then, the linker-pVII fragments and linker-pIX fragments were amplified with VCSM13 as template. The primers VII-F and VII-BW were used for linker-pVII, and primers IX-F and IX-BW for the linker-pIX construct. Finally, the $V_H$-(Gly$_4$Ser)-pVII and $V_L$-(Gly$_4$Ser)-pIX constructs were assembled through overlap extension PCR by mixing equimolar amounts of $V_H$-linker and linker-pVII fragments, or $V_L$-linker and linker-pIX fragments. The primers H1 and VII-BW were used to form the $V_H$- (Gly$_4$Ser)-pVII fragment, and the primers L1 and IX-BW were used to form the $V_L$-(Gly$_4$Ser)-pIX fragment.

After digestion with Nco I and Nhe I, the $V_H$-(Gly$_4$Ser)-pVII fragment produced using either of 21H3, 2H6, or 92H2 was ligated into phage display vector pCGMT-1b which had been pre-digested with Nco I and Nhe I.

Figure 1:
Figure 2A:
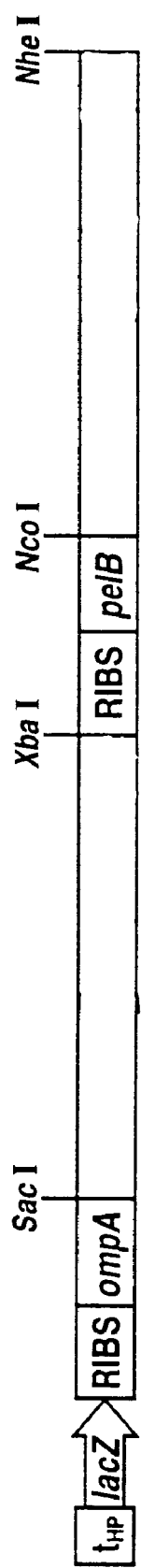
FIG. 2B illustrates the major features of dicistronic expression vector pCGMT-1b described in FIG. 2A after the $V_H$-$G_4S$-gene VII and $V_L$-$G_4S$-gene IX constructs have been inserted between the SacI/XbaI and NcoI/NheI sites, respectively, as described in the Examples.

The vector pCGMT-1b is a dicistronic expression vector that was derived from pCGMT by the addition of a ribosome binding site and ompA leader sequence to form a second expression cassette. A schematic map showing the relevant features of the pCGMT-1b vector, including restriction sites, is shown in FIG. 2A. Thus pCGMT-1b contains two ribosome binding sites and two leader sequences of ompA and pelB and can express two polypeptides off of a single transcriptional promoter (lacZ), such as immunoglobulin variable region heavy and light chains. The complete nucleotide sequence for vector pCGMT and pCGMT-1b are shown in SEQ ID NOs 19 and 20, respectively.

Figure 2B:
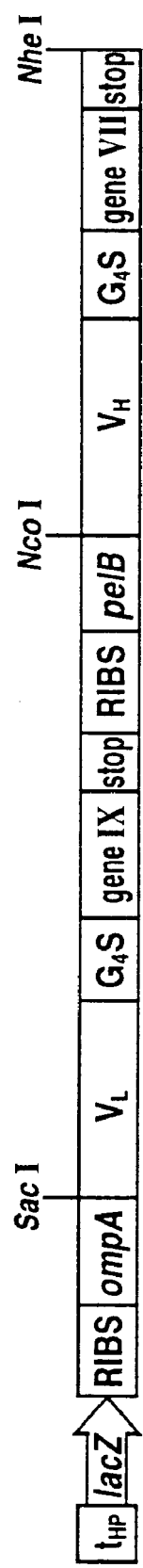

Similarly, the $V_L$-(Gly$_4$Ser)-pIX fragment produced using either of 21H3, 2H6, or 92H2 was was digested with Sac I and Nhe I and ligated into pCGMT-1b that already had the corresponding $V_H$-(Gly$_4$Ser)-pVII insert and which had been predigested with Sac I and Xba I, to form a dicistronic expression vector illustrated in FIG. 2B capable of expressing a $V_H$- (Gly$_4$Ser) -pVII/$V_L$- (Gly$_4$Ser) -pIX heterodimeric antibody.

Using the 21H3 Fab genes as starting materials, the dicistronic vector is designated as pCGMT-1b/21H3-$V_H V_L$. Using the 2H6 Fab genes the vector is designated as pCGMT-1b/2H6-$V_H V_L$, and using the 92H2 Fab genes the vector is designated as pCGMT-1b/92H2-$V_H V_L$.

The amino acid residue sequence of the various $V_H$ and $V_L$ fusion polypeptides are shown in the Sequence Listing as mature (processed) protein lacking the leader sequence as follows: 21H3 $V_H$-pVII (SEQ ID NO 27); 21H3 $V_L$-pIX (SEQ ID NO 25); 2H6 $V_H$-pVII (SEQ ID NO 31); 2H6 $V_L$-pIX (SEQ ID NO 29); 92H2 $V_H$-pVII (SEQ ID NO 35); and 92H2 $V_L$-pIX (SEQ ID NO 33).

The nucleotide sequence which encodes the amino acid residue sequence of the various $V_H$ and $V_L$ fusion polypeptides are shown in the Sequence Listing as encoding mature (processed) protein lacking the leader sequence as follows: 21H3 $V_H$-pVII (SEQ ID NO 28); 21H3 $V_L$-pIX (SEQ ID NO 26); 2H6 $V_H$-pVII (SEQ ID NO 32); 2H6 $V_L$-pIX (SEQ ID NO 30); 92H2 $V_H$-pVII (SEQ ID NO 36); and 92H2 $V_L$-pIX (SEQ ID NO 34).

2. Expression of $V_H V_L$ Heterodimeric Fusion Proteins on Phage Particles a. Propagation of Phage Particles A ligated vector produced above, such as pCGMT-1b/21H3-$V_H V_L$, is transformed into an *E.coli* host cell. Specifically the XL1-Blue *E.coli* cells (Stratagene, La Jolla, Calif.) were transformed using standard procedures with the ligated vector, and plated in agar LB medium containing 100 ug/ml carbenicillin.

The single clone of XL1-Blue cells carrying the phagemid pCGMT (containing Flag-pVII or pVII-Flag/Flag-pIX/pIX-Flag) or pCGMT-1b (containing VH-Gly4Ser-pVII and VL-Gly4Ser-pIX) was picked up and inoculate into superbroth medium containing 1% glucose, 10 $\mu$g/ml tetracycline and 100 μg/ml carbenicillin. The cells were grown at 37 C. with strong agitation (300 cycles/minute) until OD600~0.1. Helper phage VCSM13 was added into the cells at the ratio of 20~50:1 (phage:cell). The cells were grown at 37 C. for another 2 hours, and kanamycin and isopropyl beta-D-thiogalactopyranoside (IPTG) were added to final concentration of 70 μg/ml and 1 mM, respectively. The cells were then grown at 28–30 C. overnight. The phage particles released into the growth medium (cell supernatant) were harvested in the form of phage medium at that time, and used directly in phage ELISA assays, or phage particles were further concentrated by mixing the culture supernatant with one fifth volume of 20% polyethylene glycol 8000 and 3 M NaCl and incubating in ice water for 30 minutes. Precipitated phage were pelleted by centrifugation for 10 minutes, 15,000 rpm, 40 C., in a Beckman JA-17 rotor. The phage pellet was resuspended in PBS (pH 7.4) in one fiftieth of original cell culture volume.

b. ELISA to Detect Phage Expressing $V_H V_L$

The supernatant of the phage culture described above was directly used for ELISA. Microtiter wells (Corning) were coated with 25 μl of 10 μg/ml mouse anti-Flag antibody to assay Flag constructs with pVII/pIX, with PCP-BSA for 21H3 and 2H6 constructs, and with the cocaine conjugate GNC-BSA to assay the 92H2 construct. The coated plates were then incubated at room temperature overnight and blocked with 50 μl of Blotto (4% skim milk powder in PBS). Typically, 25 μl of phage supernatant was added and the plate was incubated at 37 C. for 1 hr. After washing, 25 μl of 1/1000 dilution of horseradish peroxidase/anti-M13 conjugate (Pharmacia) in Blotto was added and incubated at 37 C. for 30 minutes. The plate was extensively washed three times with PBS/0.1% tween-20 and pipetted vigorously up and down to remove nonspecific binding phage. The plate was then developed with TMB (3,3', 5,5'-tetramethylbenzidine) substrate (Pierce) and quenched with an equal volume of 2 M $H_2SO_4$. The absorbance of each reaction was then read on an ELISA Plate reader at 450 nM.

Figure 3:
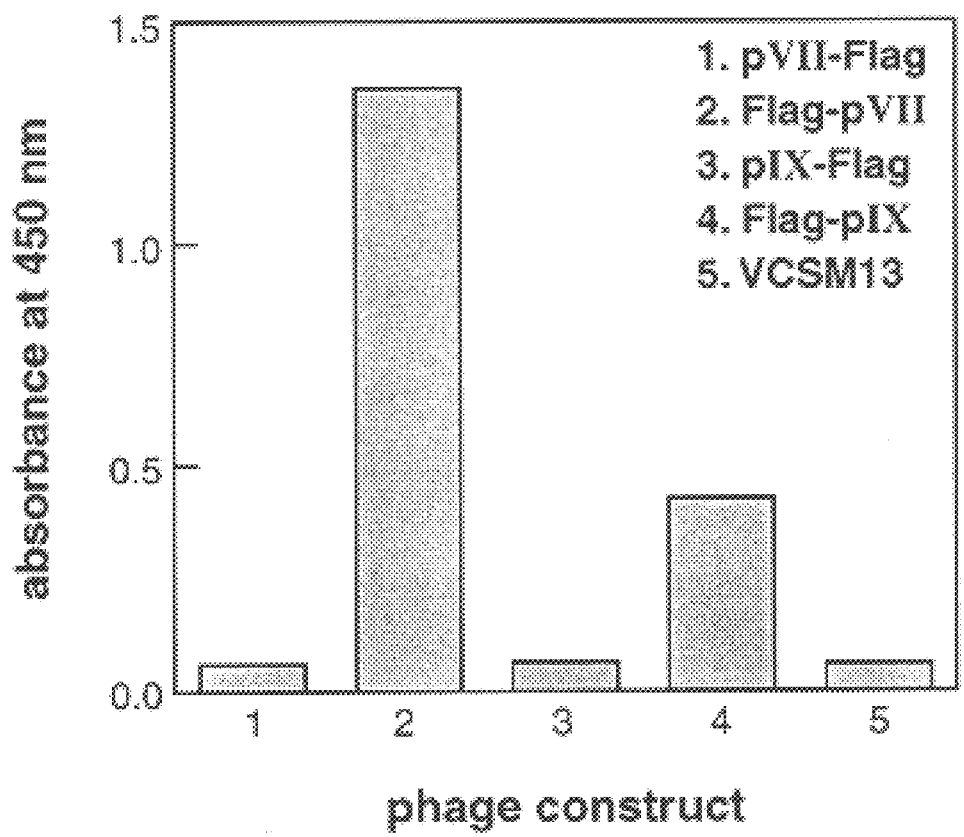
FIG. 3 illustrates the results of Phage ELISA of the different Flag and pVII or pIX fusion proteins as described in the Examples.

The results of analysis by ELISA on the Flag fusion proteins allows a determination of the orientation of expressed pVII and pIX on the Phage Particle. The present invention depends upon an understanding of the orientation of pVII or pIX on the surface of phage in order to correctly display peptides and proteins. Therefore, the octapeptide Asp-Tyr-Lys-Asp-Asp-Asp-Asp-Lys(SEQ ID NO 39), that had been widely used in protein detection and purification (Russel et al, *J.Virol.*, 63:3284–3295, 1989), was fused as a Flag tag to the N or C-terminus of pVII and pIX and inserted the constructs into a phagemid vector pCGMT. Phage particles carrying the four different fusion proteins, Flag-pVII and Flag-IX (Flag fused to the N-terminus of pVII or pIX, respectively), pVII-Flag and pIX-Flag (Flag fused to the C-terminus of pVII or pIX, respectively), were rescued from XL1-Blue cells containing those phagemid. The binding capacities of the phage particles to the monoclonal antibody anti-Flag M2 that recognized the Flag tag were tested by ELISA. As shown in FIG. 3, it is seen that only the Flag fused to the N-terminus of pVII or pIX could be detected by phage ELISA. The results indicate that the Flag peptide in these constructs was exposed on the outside of the phage coat, and therefore the N-termini of pVII and pIX must also be on the exterior of the phage particle.

Furthermore it was important to demonstrate that the display of functional Fv Fragments occurs by the interaction of pVII and pIX constructs. A principal aim of the present invention was to demonstrate that a functional heterodimeric protein could be displayed via the independent expression of pVII and pIX fusion proteins on the phage surface. Hence, in three separate examples, the heavy chains of the murine monoclonal antibodies, 21H3, 2H6 and 92H2 were constructed as fusion proteins with pVII and the comparable light chains were constructed as fusions with pIX, and the $V_H$ and $V_L$ fusion constructs were simultaneously expressed and displayed on the surface of phage particles. For negative controls, we fused only the $V_H$ of these three antibodies to pVII or the $V_L$ to pIX and omitted the other chain. The correct construction of phagemids pCGMT-1b/21H3-$V_H V_L$, pCGMT-1b/2H6-$V_H V_L$ and pCGMT-1b/92H2-$V_H V_L$ was confirmed by DNA sequencing. The phage particles that displayed antibodies 21H3, 2H6 or 92H2 were rescued from XL1-Blue cells with helper phage VCSM13.

Figure 4A:
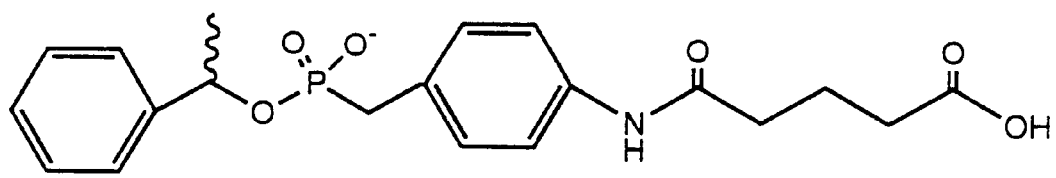
FIGS. 4A and 4B illustrate the structural formula for the PCP and GNC haptens described in the Examples.
Figure 4B:
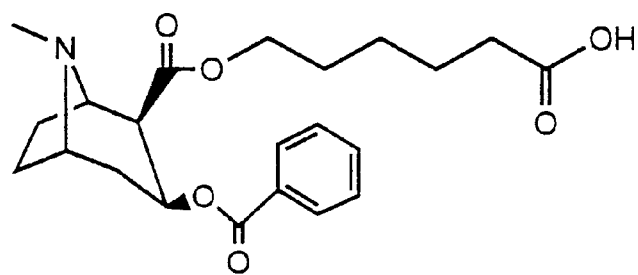

The 21H3 and 2H6 antibodies were previously shown to specifically bind to PCP-BSA conjugates, where PCP is a phosphonate hapten having the structure shown in FIG. 4A as described by Janda et al, *Science*, 244:437–440, 1989. The 92H2 antibody was previously shown to specifically bind to GNC-KLH conjugates, where GNC is a cocaine-derived hapten having the structure shown in FIG. 4B as described by Sakurai et al, *Tetrahedron Letters*, 37:5479–5482, 1996. The BSA conjugates PCP-BSA and GNC-BSA were produced using standard N-hydroxysuccinimide ester (NHS-ester) catalyzed cross-linking.

Figure 5:
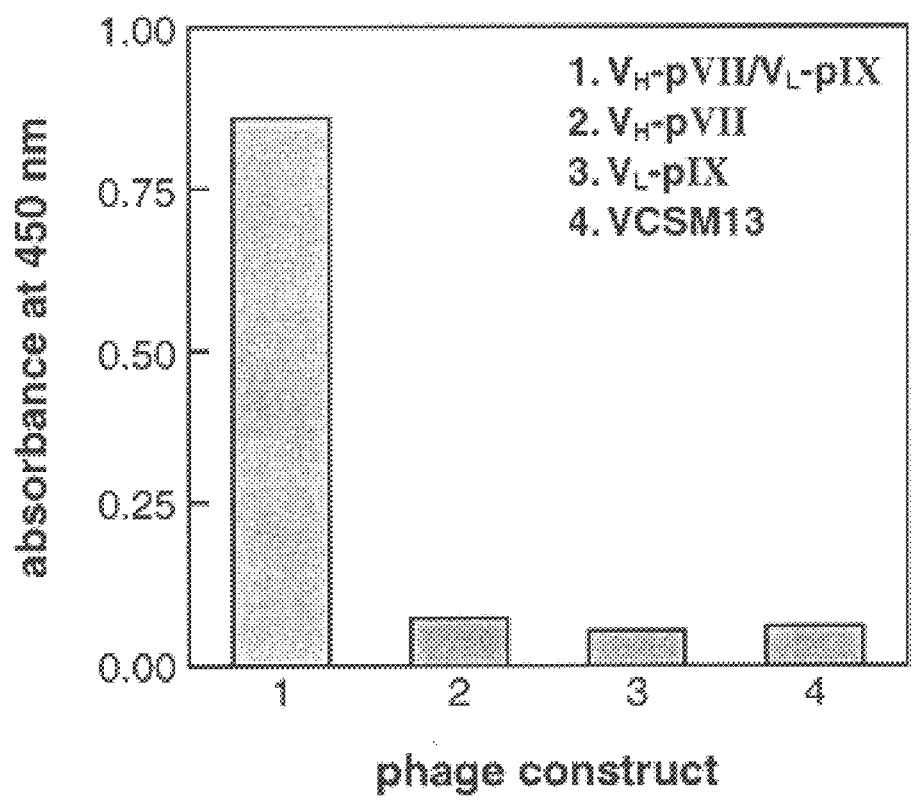
FIG. 5 illustrates the results by Phage ELISA of the antigen (PCP-BSA) binding capacities of the different fusion protein constructs of the 2H6 $V_H$ and $V_L$ with pVII and pIX as described in the Examples.

Phage ELISA showed that 21H3 and 2H6 phage antibodies specifically bound PCP-BSA and 92H2 phage antibody specifically bound GNC-BSA. A typical result for the 2H6 construct is shown (FIG. 5). For the former two antibodies, the binding activity could be inhibited by free hapten PCP and for 92H2 by cocaine. There was no binding to BSA itself. No binding activities were detected for the phage displaying only the $V_H$ or $V_L$ chains. Consequently, it was concluded that when both the $V_H$ and $V_L$ chains were displayed on the surface of phage as pVII and pIX fusion proteins, respectively, interaction of the chains occurred to form a functional Fv antibody motif.

c. Selective Enrichment of Phage by Panning

The potential for using pVII and pIX displayed Fv fragments in selection and evolution experiments was demonstrated by selection enrichment of one species of antibody from a mixture of two antibodies based on function. The 2H6 and 92H2 phage Fvs were used for the experiment because they had similar cell densities under the same growth conditions. The 21H3 gene was more toxic to XL1-Blue cells and showed a much lower cell density.

The 2H6 phage was diluted into 92H2 phage at a ratio of 1:100 or 1:10⁸, and the mixture was used for selection against PCP-BSA. In another experiment, the 92H2 phage were mixed with 2H6 at a ratio of 1:100 and the mixture was used for selection against GNC-BSA. Microtiter plates (Corning) were coated overnight at room temperature with 25 μl/well of the PCP-BSA or GNC-BSA conjugate (10 μg/ml in PBS). After washing 5 times with water, the wells were blocked with 4% of milk in PBS at 37 C. for 1 hr. Then, 50 μl ($10^{12}$ cfu/well) of phage mixture (prepared as described above) was added and incubated for 1 hour at 37 C. The plate was washed 20 times with PBS/0.1% Tween-20 and 10 times with PBS. The bound phage were then eluted with 50 μl/well of elution buffer (0.1 M HCl/Glycine/0.1% BSA, pH 2.2). After 10 min, the elution buffer was removed and neutralized with 3 μl of 2 M Tris-base per well. Phage eluted from first round of selection were used to infect *E. coli* XL1-Blue cells. Phage particles were rescued from the cells and used for the subsequent round of antigen selections.

In a first panning experiment, the enrichment was tested by mixing 2H6 phage Fv and 92H2 phage Fv at a ratio of 1:100 or 100:1 followed by selection against PCP-BSA or GNC-BSA. After one round of panning, 9 of 10 randomly selected clones were 2H6 phage Fv when mixed at a ratio of 1:100 and selected against PCP-BSA, and 6 of 10 clones were found to be 92H2 phage Fv when mixed at a ratio of 1:100 and selected against GNC-BSA. The results showed that at least a 100-fold enrichment could be achieved per round of panning when a functional Fv fragment was displayed on the phage surface as a result of the interaction of pVII and pIX constructs.

In a second panning experiment, selection from a highly dilute mixture was examined. The 2H6 phage Fv were mixed with 92H2 phage Fv at a ratio of $1:10^8$ and panned against immobilized PCP-BSA. The panning was performed for a total of two rounds. After each round of panning, the phage were pooled and tested by ELISA for their ability to bind PCP-BSA and GNC-BSA. The phage mixture before panning showed no binding activity to PCP-BSA and strong binding to GNC-BSA. However, after two rounds of selection, phage showed greatly enhanced binding to PCP-BSA and weak binding to GNC-BSA (FIG. 6). To verify the ratio of 2H6 and 92H2 clones before and after each round of panning, phage were rescued from 15 randomly selected clones and tested by ELISA for their ability to bind PCP-BSA and GNC-BSA. Of the 15 clones, the number of 2H6 clones increased from 7 after first round of panning to 15 after the second round of panning. In contrast, of 15 clones randomly selected from the unpanned phage mixture, none were 2H6. The results showed that a $10^8$-fold enrichment was accomplished after only two rounds of panning.

3. Assays to Measure Activity of Catalytic Antibodies

Reactions to measure catalytic activity of an expressed $V_H V_L$ fusion protein heterodimer were carried out in 100 mM Bicine (N,N-bis(2-hydroxyethyl)glycine), pH 8.5, containing 10% DMSO (dimethylsulfoxide) as cosolvent. Approximately 150 nM 21H3 phage ($1 \times 10^{14}$ cfu/ml) in 100 mM Bicine, pH 8.5 was mixed with 5 mM (S)-(-)-sec-phenethyl alcohol and 16 mM vinyl 4-acetamidophenylacetate prepared as stock solutions in DMSO. A 50 ul aliquot was removed every 30 min and quenched by adding 4 ul of 10% $HClO_4$. The formation of the product (S)-(-)-sec-phenethyl 4-acetamidophenylacetate was monitored using reversed-phase HPLC [C18-VYDAC 201TP54 column; isocratic mobile phase (62% water-0.1% TFA/38% acetonitrile); 1.75 ml/min; 254 nm].

In the case of the 21H3 phage Fv, the catalytic activity was investigated and compared to our previously studied 21H3 IgG antibody (Wirsching et al, Science, 252:680–685, 1991). When 150 nM of the phage antibody ($1 \times 10^{14}$ cfu/ml) was mixed with 5 mM alcohol and 16 mM vinyl ester, the product ester could be detected within 30 min (data not shown). A comparison of time course curves showed that the catalytic activity from 150 nM phage Fv was roughly equal to 50 nM of the 21H3 IgG.

4. Characterization of Expressed $V_H V_L$ Proteins a. Analysis of Dissociation of $V_H$ and $V_L$ Fusion Proteins on the Surface of Phage Particle To verify that the Fv antibody on phage surface was really displayed through both pVII and pIX by association of the $V_H$ and $V_L$ fusion proteins, $5 \times 10^{13}$ cfu of Fv antibody phage in 1.5 ml was treated with 0.1% Sarkosyl in PBS for 20 hr and loaded onto a HIPrep TM 26/60 Sephacryl S-100HR gel filtration column (Pharmacia) preequilibrated with PBS containing 0.1% Sarkosyl. The phage fraction was collected, precipitated with polyethylene glycol (PEG), and dialyzed into PBS without Sarkosyl. The antigen binding activity of 21H3 was tested before and after the Sarkosyl treatment by phage ELISA.

In previous work, $V_H$ and $V_L$ domains were found to associate and form an antigen binding site on the phage surface (Ito et al, J. Biochem (Tokyo), 123:832–838, 1998). Though unlikely in the present experiments, the possibility existed that while one variable domain was displayed on the phage surface as the intended pVII or pIX fusion protein, the other domain existed as a free chain and associated with the first in the periplasmic space. To verify that the Fv on the phage surface resulted through interaction of both pVII and pIX fusion proteins, the 21H3 phage Fv was treated with 0.1% Sarkosyl in PBS at room temperature for 20 h and purified by gel filtration. Sarkosyl, a relatively mild detergent, has frequently been used for dissolving precipitates of phage particles and was successfully used to dissociate Fv fragments (Ito et al, J. Biochem (Tokyo), 123:832–838, 1998). The phage fraction was collected and dialyzed against PBS to remove the Sarkosyl. The antigen binding activity of 21H3 was tested by phage ELISA before and after the Sarkosyl treatment and no difference was observed (data not shown).

b. Electron Microscopy to Evaluate the Surface Expression of $V_H V_L$ on Phage Particles The specific binding of phage Fv s to their antigen labeled with 5 nm colloidal gold, was directly visualized by electron microscopy. Stable complexes of 5 nm gold particles bound to PCP-BSA were prepared according to known methodology (Horisberger et al, J. Histochem. Cytochem., 25:295–305, 1977; Slot et al, Eur. J. Cell Biol., 38:87–93, 1985). The designation PCP referred to the phosphonate hapten originally used to obtain the antibodies 21H3 and 2H6 (Janda et al, Science, 244:437–440, 1989). To ensure the removal of any unbound protein, the complexes were centrifuged through a 7% glycerol cushion at the speed of 55,000 rpm for 1.5 hr as described (Slot et al, Eur. J. Cell Biol., 38:87–93, 1985). The pelleted complexes were resuspended in PBS (phosphate-buffered saline; 10 mM phosphate, 150 mM NaCl, pH 7.4) containing 0.1% BSA (bovine serum albumin) and stored at 4° C. Phage were prepared by 1 mM IPTG induction at 30° C. overnight, precipitated by PEG and diluted into PBS containing 0.01% BSA to a final concentration of $5 \times 10^{10}$ cfu/ml. A 2 $\mu l$ aliquot of the diluted phage was applied to Formvar coated nickel grids (200 mesh) for 5 min. Unbound phage were removed by washing with PBS and then 1% BSA in PBS for 10 min. PCP-BSA-gold complexes were applied to the grids undiluted. After 30 min, the grids were washed with PBS, then stained with 1% uranyl acetate for visualization by electron microscopy. Randomly selected areas on the grids were photographed in order to quantify the number of gold particles associated with phage.

The specific binding of phage Fv s to their antigen labeled with 5 nm colloidal gold, was directly visualized by electron microscopy. Examination of filamentous phage 21H3 and 2H6 revealed specific labeling by the PCP-BSA-gold complex at one end of the phage (FIG. 7A, FIG. 7B). It was observed that some of the phage were labeled by more than one gold particle (FIG. 7B). The specificity of the labeling to 21H3 and 2H6 phage was indicated by the absence of labeling using a BSA-gold complex, and also that 92H2 phage could not be labeled by the PCP-BSA gold complex (data not shown).

C. Competition ELISA Assay

A competitive ELISA assay is conducted using the 92H2 and 2H6 phage to evaluate the nature of the antibody binding specificity. To that end, 96-well microtiter plates were coated with 25 µl of 10 µg/ml PCP-BSA for assay to PCP2H6 construct and GNC-BSA for 92H2 construct. The phage Fv antibodies were titrated by serial dilution to determine the proper concentration of phage antibodies for inhibition ELISA. Varying concentrations of free hapten of PCP (for 2H6) and GNC (for 92H2) were then incubated with the proper concentration of phage antibodies at 37 C. for 5 minutes. This mixture was then applied to the microtiter plates and incubated at 37 C. for 1 hr and developed as described above for ELISA.

5. Discussion of Examples 1–4

Although it had been previously suggested that pVII and pIX were not functional with another protein fused to their N-termini (Endemann et al, *J. Mol. Biol.*, 250:496–506, 1995), the present results demonstrate that such fusions were viable. With the present results it is seen that pVII or pIX, or both are applicable to combinatorial phage display protocols utilizing highly diverse protein sequences.

The specific gold labeling of phage Fv determined from electron microscopy clearly showed the presence of gold at one end of the phage particle. Interestingly, phage that harbored either one or two gold labels were observed. It is presumed that the latter resulted from the bivalent display of Fv fragments, rather than multiple gold labeling of PCP-BSA. Approximately 20% of the phage were labeled by gold and therefore displayed a functional Fv antibody. However, the kinetic analysis showed that the activity of 150 nM 21H3 phage Fv was equal to the activity of 50 nM 21H3 IgG. The data taken together, along with the assumption that the specific activities of the Fv and IgG were comparable, suggested some phage particles simultaneously displayed more than one Fv fragment.

Fv fragments are heterodimers made up of $V_H$ and $V_L$ domains and are the smallest antibody fragments that contain all the information necessary for specific antigen binding. However, the noncovalently associated chains in an isolated Fv fragment are not highly stable and tend to dissociate (Glockshuber et al, *Biochemistry*, 29:1362–1367, 1990). Known methods for stabilizing Fv fragments are as single chain Fvs (scFvs) (Rodi et al, *Curr. Opin. Biotechnol.*, 10:87–93, 1999) and as disulfide-stabilized Fvs (dsFvs) (Bird et al, *Science*, 242:423–426, 1988). Yet, scFvs are still often unstable and can have lower affinities compared to Fabs and whole IgG because the linker interferes with binding or does not sufficiently stabilize the heterodimer. While the dsFvs are generally more stable and without a linker, they require the incorporation of a disulfide into the library construction. In addition, it is likely that dsFv libraries cover a biased antibody subset in which the interchain disulfide does not interfere with antigen binding (Brinkmann et al, *J. Immunol. Methods*, 182:41–50, 1995). The Fv antibody displayed by pVII and pIX in our format can be viewed as a phage-stabilized Fv (psFv) that mimics the natural antibody structure without the disadvantages of scFvs and dsFvs. Our Fvs retain affinity and are robust in that each chain is independently anchored to the phage coat.

Most important, our new format would be particularly useful for the combinatorial display of heterodimeric arrays. Furthermore, while the reasons are not yet clear, this format appears to yield a particularly powerful enrichment during panning protocols. The pVII and pIX are apparently in close enough proximity such that fusion proteins with the $V_H$ and $V_L$ of an antibody are able to form a functional heterodimer. It is believed that the approach can be extended to the display of diverse polypeptides for the creation of artificial antibodies. The ability to display a large repertoire of novel dimeric binding domains unconstrained by the specific programming of antibody structure will increase our understanding of protein-protein interactions and potentially lead to the discovery of unique biological activities.

6. Preparation of a Single Chain Fv Fusion Protein

As a demonstration of the versatility of the present invention, a single chain antibody (scFv) based on the Fv portions of an the 21H3 heavy and light chains was constructed. To that end, the relevant portions of the $V_H$ and $V_L$ genes for the 21H3 antibody were amplified by PCR, and fused with a $(Gly_4Ser)$ 3 (SEQ ID NO 37, from 125–139) linker encoding sequence by overlapping PCR, and further fused with a $(Gly_4Ser)$ linker to the pIX gene by overlapping PCR to form the scFv construct designated scFV-21H3-pIX in which the components are arranged as $V_H$-$(GlY_4Ser)_3$-$V_L$-$(Gly_4Ser)$-pIX. The amino acid residue sequence of the fusion protein is shown in SEQ ID NO 37, and the nucleotide sequence coding the fusion protein is shown in SEQ ID NO 38. The resulting construct was transformed into *E.coli* as described above, phage particles were similarly prepared, and the expressed scFV-21H3-pIX fusion protein on phage particles was evaluated in the phage ELISA described hereinabove. By ELISA, the single chain 21H3 antibody fusion to pIX was strongly reactive with the PCP-BSA conjugate when compared to wild-type phage (VCSM13) as shown in FIG. 8.

The invention has been described in the above examples using a variety of formulations, although it should be apparent that various other carrier agents that are compatible with the probiotic compositions may be substituted in the examples to give similar results. Accordingly, the invention may be embodied in other specific forms without departing from it in spirit. The examples are to be considered in all respects only as illustrative and not as restrictive, and the scope of the invention is indicated by the claims that follow. All modifications which come within the meaning and range of the lawful equivalency of the claims are to be embraced within their scope.

SEQUENCE LISTING

SEQ ID NO 1 VII-FOR:
(5'-CTATCCATGGCAATGGAGCAGGTCGCGGATTTC-3')

SEQ ID NO 2 VII-fBW
(5'-ATTTAGCTAGCTTATTTGTCATCGTCATCTTTGTAGTC
TCTTTGACCCCCAGCGATTAT-3');

SEQ ID NO 3 VII-fFOR
(5'-CTATCCATGGCAGACTA CAAAGATGACGATGACAAAA
TGGAGCAGGTCGCGGATTTC-3'

SEQUENCE LISTING

SEQ ID NO 4 VII-BW
(5'-GATTTAGCTAGCTTATTATCTTTGACCCCCAGCGATTAT-3');

SEQ ID NO 5 IX-FOR
(5'-CTATCCATGGCAATGAGTGTTTTAGTGTATTCT-3')

SEQ ID NO 6 IX-fBW
(5'-ATTTAGCTAGCTTATTTGTCATCGTCATCTTTGTAGTCTG
AGGAAGTTTCCATTAAACG-3');

SEQ ID NO 7 IX-fFOR
(5'-CTATCCATGGCAGACTACAAAGATGACGATGACAAAATG
AGTGTTTTAGTGTATTCT-3')

SEQ ID NO 8 IX-BW
(5'-GATTTAGCTAGCTTATTATGAGGAAGTTTCCATTAAACG-3')

SEQ ID NO 9 H1
(5'-GCCTACGGCAGCCGCTGGATTGTTATTACT-3')

SEQ ID NO 10 H2
(5'-GCCAGAACCAC CACCAGAGACAGTGACCAG-3')

SEQ ID NO 11 H3
(5'-GCCAGAACCACCACCAGAGACGGTGA CTGAGGTTCC-3')

SEQ ID NO 12 H4
(5'-GCCAGAACCACCACCAGATGAGGAAACGGTGACCGT-3')

SEQ ID NO 13 L1
(5'-GCTATCGCGATTGCTGTGGCACTGGCTGGT-3')

SEQ ID NO 14 L2
(5'-GGAGCCGCCGCCGCCAGAATCAGCCCGTTTGATTTC-3')

SEQ ID NO 15 L3
(5'-GGAGCCGCCGCCGCCAGAATCAGTCCGTTTCAACTC-3')

SEQ ID NO 16 L4
(5'-GGAGCCGCCGCCGCCAGAGACCAGGCCCCGAGGCC-3')

SEQ ID NO 17 VIIF
(5'-TCTGGTGGTGGTTCTGGCATGGAGCAGGTCGCGATTTC-3')

SEQ ID NO 18 IXF
(5'-TCTGGCGGCGGCGGCTCCATGAGTGTTTTAGTGTATTCT-3')

SEQ ID NO 19 pCGMT
GGGAAATTGTAAGCGTTAATATTTTGTTAAAATTCGCGTTAAATTTTTGTTAAATCAGC

TCATTTTTTAACCAATAGGCCGAAATCGGCAAAATCCCTTATAAATCAAAAGAATAGAC

CGAGATAGGGTTGAGTGTTGTTCCAGTTTGGAACAAGAGTCCACTATTAAAGAACGTGG

ACTCCAACGTCAAAGGGCGAAAAACCGTCTATCAGGGCGATGGCCCACTACGTGAACCA

TCACCCTAATCAAGTTTTTTGGGGTCGAGGTGCCGTAAAGCACTAAATCGGAACCCTAA

AGGGAGCCCCCGATTTAGAGCTTGACGGGGAAAGCCGGCGAACGTGGCGAGAAAGGAAG

GGAAGAAAGCGAAAGGAGCGGGCGCTAGGGCGCTGGCAAGTGTAGCGGTCACGCTGCGC

GTAACCACCACACCCGCCGCGCTTAATGCGCCGCTACAGGGCGCGTCAGGTGGCACTTT

TCGGGGAAATGTGCGCGGAACCCCTATTTGTTTATTTTTCTAAATACATTCAAATATGT

ATCCGCTCATGAGACAATAACCCTGATAAATGCTTCAATAATATTGAAAAAGGAAGAGT

ATGAGTATTCAACATTTCCGTGTCGCCCTTATTCCCTTTTTTGCGGCATTTTGCCTTCC

TGTTTTTGCTCACCCAGAAACGCTGGTGAAAGTAAAAGATGCTGAAGATCAGTTGGGTG

CACGAGTGGGTTACATCGAACTGGATCTCAACAGCGGTAAGATCCTTGAGAGTTTTCGC

CCCGAAGAACGTTTTCCAATGATGAGCACTTTTAAAGTTCTGCTATGTGGCGCGGTATT

SEQUENCE LISTING

```
ATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTGAC

AACGATCGGAGGACCGAAGGAGCTAACCGCTTTTTTGCACAACATGGGGGATCATGTAA

CTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACT

TACTCTAGCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCCCTCCCGTAT

CGTAGTTATCTACACGACGGGGAGTCAGGCAACTATGGATGAACGAAATAGACAGATCG

CTGAGATAGGTGCCTCACTGATTAAGCATTGGTAACTGTCAGACCAAGTTTACTCATAT

ATACTTTAGATTGATTTAAAACTTCATTTTTAATTTAAAAGGATCTAGGTGAAGATCCT

TTTTGATAATCTCATGACCAAAATCCCTTAACGTGAGTTTTCGTTCCACTGAGCGTCAG

ACCCCGTAGAAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAAATACTGTCC

TTCTAGTGTAGCCGTAGTTAGGCCACCACTTCAAGAACTCTGTAGCACCGCCTACATAC

CTCGCTCTGCTAATCCTGTTACCAGTGGCTGCTGCCAGTGGCGATAAGTCGTGTCTTAC

CGGGTTGGACTCAAGACGATAGTTACCGGATAAGGCGCAGCGGTCGGGCTGAACGGGGG

GTTCGTGCACACAGCCCAGCTTGGAGCGAACGACCTACACCGAACTGAGATACCTACAG

CGTGAGCTATGAGAAAGCGCCACGCTTCCCGAAGGGAGAAAGGCGGACAGGTATCCGGT

AAGCGGCAGGGTCGGAACAGGAGAGCGCACGAGGGAGCTTCCAGGGGGAAACGCCTGGT

ATCTTTATAGTCCTGTCGGGTTTCGCCACCTCTGACTTGAGCGTCGATTTTTGTGATGC

TCGTCAGGGGGCGGAGCCTATGGAAAAACGCCAGCAACGCGGCCTTTTTACGGTTCCT

GGCCTTTTGCTGGCCTTTTGCTCACATGTTCTTTCCTGCGTTATCCCCTGATTCTGTGG

ATAACCGTATTACCGCCTTTGAGTGAGCTGATACCGCTCGCCGCAGCCGAACGACCGAG

CGCAGCGAGTCAGTGAGCGAGGAAGCGGAAGAGCGCCCAATACGCAAACCGCCTCTCCC

CGCGCGTTGGCCGATTCATTAATGCAGGGTACCCGATAAAAGCGGCTTCCTGACAGGAG

GCCGTTTTGTTTTGCAGCCCACCTCTGGCACGACAGGTTTCCCGACTGGAAAGCGGGCA

GTGAGCGCAACGCAATTAATGTGAGTTAGCTCACTCATTAGGCACCCCAGGCTTTACAC

TTTATGCTTCCGGCTCGTATGTTGTGTGGAATTGTGAGCGGATAACAATTCAATTCAGG

AGGAATTTAAAATGAAATACCTATTGCCTACGGCAGCCGCTGGATTGTTATTACTCGCG

GCCCAGCCGGCCATGGCAAAGCTTGGATCCGATATCCATATGGGCCTCGGGGCCTGGT

CGACTACAAAGATGACGATGACAAATAGACTAGTGGCCAGGAGGGTGGTGGCTCTGAGG

GTGGCGGTTCTGAGGGTGGCGGCTCTGAGGGAGGCGGTTCCGGTGGTGGCTCTGGTTCC

GGTGATTTTGATTATGAAAAGATGGCAAACGCTAATAAGGGGCTATGACCGAAAATGC

CGATGAAAACGCGCTACAGTCTGACGCTAAAGGCAAACTTGATTCTGTCGCTACTGATT

ACGGTGCTGCTATCGATGGTTTCATTGGTGACGTTTCCGGCCTTGCTAATGGTAATGGT

GCTACTGGTGATTTTGCTGGCTCTAATTCCCAAATGGCTCAAGTCGGTGACGGTGATAA
```

-continued

SEQUENCE LISTING

TTCACCTTTAATGAATAATTTCCGTCAATATTTACCTTCCCTCCCTCAATCGGTTGAAT

GTCGCCCTTTTGTCTTTAGCGCTGGTAAACCATATGAATTTTCTATTGATTGTGACAAA

ATAAACTTATTCCGTGGTGTCTTTGCGTTTCTTTTATATGTTGCCACCTTTATGTATGT

ATTTTCTACGTTTGCTAACATACTGCGTAATAAGGAGTCTTAAGCTAGCTAATTAATTT

AAGCGGCCGCAGATCT

SEQ ID NO 20 pCMGT-1b
GGGAAATTGTAAGCGTTAATATTTTGTTAAAATTCGCGTTAAATTTTTGTTAAATCAGC

TCATTTTTTAACCAATAGGCCGAAATCGGCAAAATCCCTTATAAATCAAAAGAATAGAC

CGAGATAGGGTTGAGTGTTGTTCCAGTTTGGAACAAGAGTCCACTATTAAAGAACGTGG

ACTCCAACGTCAAAGGGCGAAAAACCGTCTATCAGGGCGATGGCCCACTACGTGAACCA

TCACCCTAATCAAGTTTTTTGGGGTCGAGGTGCCGTAAAGCACTAAATCGGAACCCTAA

AGGGAGCCCCCGATTTAGAGCTTGACGGGGAAAGCCGGCGAACGTGGCGAGAAAGGAAG

GGAAGAAAGCGAAAGGAGCGGGCGCTAGGGCGCTGGCAAGTGTAGCGGTCACGCTGCGC

GTAACCACCACACCCGCCGCGCTTAATGCGCCGCTACAGGGCGCGTCAGGTGGCACTTT

TCGGGGAAATGTGCGCGGAACCCCTATTTGTTTATTTTTCTAAATACATTCAAATATGT

ATCCGCTCATGAGACAATAACCCTGATAAATGCTTCAATAATATTGAAAAAGGAAGAGT

ATGAGTATTCAACATTTCCGTGTCGCCCTTATTCCCTTTTTTGCGGCATTTTGCCTTCC

TGTTTTTGCTCACCCAGAAACGCTGGTGAAAGTAAAAGATGCTGAAGATCAGTTGGGTG

CACGAGTGGGTTACATCGAACTGGATCTCAACAGCGGTAAGATCCTTGAGAGTTTTCGC

CCCGAAGAACGTTTTCCAATGATGAGCACTTTTAAAGTTCTGCTATGTGGCGCGGTATT

ATCCCGTATTGACGCCGGGCAAGAGCAACTCGGTCGCCGCATACACTATTCTCAGAATG

ACTTGGTTGAGTACTCACCAGTCACAGAAAAGCATCTTACGGATGGCATGACAGTAAGA

GAATTATGCAGTGCTGCCATAACCATGAGTGATAACACTGCGGCCAACTTACTTCTGAC

AACGATCGGAGGACCGAAGGAGCTAACCGCTTTTTTGCACAACATGGGGGATCATGTAA

CTCGCCTTGATCGTTGGGAACCGGAGCTGAATGAAGCCATACCAAACGACGAGCGTGAC

ACCACGATGCCTGTAGCAATGGCAACAACGTTGCGCAAACTATTAACTGGCGAACTACT

TACTCTAGCTTCCCGGCAACAATTAATAGACTGGATGGAGGCGGATAAAGTTGCAGGAC

CACTTCTGCGCTCGGCCCTTCCGGCTGGCTGGTTTATTGCTGATAAATCTGGAGCCGGT

GAGCGTGGGTCTCGCGGTATCATTGCAGCACTGGGGCCAGATGGTAAGCCCTCCCGTAT

CGTAGTTATCTACACGACGGGGAGTCAGGCAACTATGGATGAACGAAATAGACAGATCG

CTGAGATAGGTGCCTCACTGATTAAGCATTGGTAACTGTCAGACCAAGTTTACTCATAT

ATACTTTAGATTGATTTAAAACTTCATTTTTAATTTAAAAGGATCTAGGTGAAGATCCT

TTTTGATAATCTCATGACCAAAATCCCTTAACGTGAGTTTTCGTTCCACTGAGCGTCAG

ACCCCGTAGAAAAGATCAAAGGATCTTCTTGAGATCCTTTTTTTCTGCGCGTAATCTGC

TGCTTGCAAACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAAATACTGTCC

TTCTAGTGTAGCCGTAGTTAGGCCACCACTTCAAGAACTCTGTAGCACCGCCTACATAC

CTCGCTCTGCTAATCCTGTTACCAGTGGCTGCTGCCAGTGGCGATAAGTCGTGTCTTAC

CGGGTTGGACTCAAGACGATAGTTACCGGATAAGGCGCAGCGGTCGGGCTGAACGGGGG

SEQUENCE LISTING

```
GTTCGTGCACACAGCCCAGCTTGGAGCGAACGACCTACACCGAACTGAGATACCTACAG
CGTGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATGC
TCGTCAGGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCTGTGG
ATAACCGTATTACCGCCTTTGAGTGAGCTGATACCGCTCGCCGCAGCCGAACGACCGAG
CGCAGCGAGTCAGTGAGCGAGGAAGCGGAAGAGCGCCCAATACGCAAACCGCCTCTCCC
CGCGCGTTGGCCGATTCATTAATGCAGGGTACCCGATAAAAGCGGCTTCCTGACAGGAG
GCCGTTTTGTTTTGCAGCCCACCTCTGGCACGACAGGTTTCCCGACTGGAAAGCGGGCA
GTGAGCGCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTGAATTCAGG
AGGAATTTAAAATGAAAAAGACAGCTATCGCGATTGCAGTGGCACTGGCTGGTTTCGCT
ACCGTGGCCCAGGCGGCCGAGCTCATGCATTCTAGATAATTAATTAGGAGGAATTTAAA
ATGAAATACCTATTGCCTACGGCAGCCGCTGGATTGTTATTACTCGCTGCCCAACCAGC
CATGGCCGAGGTGCAGCTGCTCGAGGGATCCACTAGTGGCCAGGCCGGCCAGGAGGGTG
GTGGCTCTGAGGGTGGCGGTTCTGAGGGTGGCGGCTCTGAGGGAGGCGGTTCCGGTGGT
GGCTCTGGTTCCGTGATTTTGATTATGAAAAGATGGCAAACGCTAATAAGGGGCTAT
GACCGAAAATGCCGATGAAAACGCGCTACAGTCTGACGCTAAAGGCAAACTTGATTCTG
TCGCTACTGATTACGGTGCTGCTATCGATGGTTTCATTGGTGACGTTTCCGGCCTTGCT
AATGGTAATGGTGCTACTGGTGATTTGCTGGCTCTAATTCCCAAATGGCTCAAGTCGG
TGACGGTGATAATTCACCTTTAATGAATAATTTCCGTCAATATTTACCTTCCCTCCCTC
AATCGGTTGAATGTCGCCCTTTTGTCTTTAGCGCTGGTAAACCATATGAATTTTCTATT
GATTGTGACAAAATAAACTTATTCCGTGGTGTCTTTGCGTTTCTTTTATATGTTGCCAC
CTTTATGTATGTATTTTCTACGTTTGCTAACATACTGCGTAATAAGGAGTCTTAAGCTA
GCTAATTAATTTAAGCGGCCGCAGATCT
```

SEQ ID NO 21 pVII .aa
MEQVADFDTIYQAMIQISVVLCFALGIIAGGQR*

SEQ ID NO 22 gVII .seg
ATGGAGCAGGTCGCGGATTTCGACACAATTTATCAGGCGATGATACAAATCTCCGTTGT

ACTTTGTTTCG CGCTTGGTATAATCGCTGGGGGTCAAAGATGA

SEQ ID NO 23 pIX .aa
MSVLVYSFASFVLGWCLRSGITYFTRLMETSS*

SEQ ID NO 24 gIX .seq
ATAGATGTTTTAGTGTATTCTTTCGCCTCTTTCGTTTTAGGTTGGTGCCTTCGTAGTGG

CATTACGTATTTTACCCGTTTAATGGAAACTTCCTCATGA

SEQ ID NO 25 21h3 VL pIX .aa
DIQMTQSPSSLSASLGERVSLTCRASQEISGYLYWLQQKPDGTIKRLIYAASTLDSGVP

KRFSGSRSGSDYSLTISSLESEDFADYYCLQYASYPRTFGGGTKVEIKRADSGGGGSMS

VLVYSFASFVLGWCLRSGITYF TRLMETSS*

SEQ ID NO 26 21h3 VL gIX .seq

SEQUENCE LISTING

```
GATATCCAAATGACACAATCTCCATCCTCCTTATCTGCCTCTCTGGGAGAAAGAGTCAG

TCTCACTTGTCGGGCAAGTCAGGAGATTAGTGGTTACTTATACTGGCTTCAGCAGAAAC

CAGATGGAACTATTAAACGCCTGATCTACGCCGCATCCACTTTAGATTCTGGTGTCCCA

AAAAGGTTCAGTGGCAGTAGGTCTGGGTCAGATTATTCTCTCACCATCAGCAGCCTTGA

GTCTGAAGATTTTGCAGACTATTACTGTCTACAATATGCTAGTTATCCTCGGACGTTCG

GTGGAGGCACCAAGGTTGAAATCAAACGGGCTGATTCTGGCGGCGGCGGCTCCATGAGT

GTTTTAGTGTATTCTTTCGCCTCTTTCGTTTTAGGTTGGTGCCTTCGTAGTGGCATTAC

GTATTTTACCGTTTAATGGAAACTTCCTCATAATAAGCTAGC

SEQ ID NO 27  21h3 VH pVII  .aa
MAEVQLLEVQLQQSGPVLVKPGGSVKMSCKASEYTLTSYLFQWVKQKSGQGLEWIGYIY

PYNGGTRYNEKFRGKATLTSDKSSNTAYLELSSLTSEDSAVYYCARSSMSDPGANWGPG

TLVTVSGGGGSGMEQVADFDTIYQAMIQISVVLCFALGIIAGGQR*

SEQ ID NO 28  21h3 VH gVII  .seq
ATGGCCGAGGTGCAGCTGCTCGAGGTCCAGCTGCAACAATCTGGACCTGTGCTGGTAAA

GCCTGGGGGTTCAGTGAAAATGTCCTGCAAGGCTTCTGAATACACACTCACTTCTTATC

TTTTTCAGTGGGTGAAGCAGAAGTCAGGGCAGGGCCTTGAGTGGATTGGATATATTTAT

CCTTACAATGGTGGTACTCGGTACAATGAGAAGTTCAGAGGCAAGGCCACACTGACTTC

AGACAAGTCCTCCAACACAGCCTACTTGGAACTCAGCAGCCTGACCTCTGAAGACTCTG

CAGTCTATTACTGTGCAAGATCTAGTATGAGTGACCCCGGGGCTAACTGGGGCCCAGGG

ACTCTGGTCACTGTCTCTGGTGGTGGTGGTTCTGGCATGGAGCAGGTCGCGGATTTCGA

CACAATTTATCAGGCGATGATACAAATCTCCGTTGTACTTTGTTTCGCGCTTGGTATAA

TCGCTGGGGGTCAAAGAT AATAAGCTAGC

SEQ ID NO 29  2h6 VL pIX  .aa
VLTQSPAIMYASPGEKVTITCSASSSVSYMHWFQQKPGTSPKLWIYSTSKLASGVAPARF

SGSGSGTSYSLTISRMEADEDVATYYCQQRSSYTVTFGAGTKLELKRTSGGGGSMSVLVY

SFASFVLGWCLRSGITYFTRLM ETSS*

SEQ ID NO 30  2h6 VL gIX  .seq
GTGCTCACCCAGTCTCCAGCAATCATGTATGCATCTCCAGGGGAGAAGGTCACCATAAC

CTGCAGTGCCAGCTCAAGTGTAAGTTACATGCACTGGTTCCAGCAGAAGCCAGGCACTT

CTCCCAAACTCTGGATTTATAGCACATCCAAGCTGGCTTCTGGAGTCCCTGCTCGCTTC

AGTGGCAGTGGATCTGGGACCTCTTACTCTCTCACAATCAGCCGAATGGAGGCTGAAGA

TGTTGCCACTTATTACTGCCAGCAAAGGAGCAGTTATACGGTCACGTTCGGTGCTGGGA

CCAAGCTGGAGTTGAAACGGACTTCTGGCGGCGGCGGCTCCATGAGTGTTTTAGTGTAT

TCTTTCGCCTCTTTCGTTTTAGGTTGGTGCCTTCGTAGTGGCATTACGTATTTTACCCG

TTTAATGGAAACTTCCTCATAATAAGCTAG

SEQ ID NO 31  2h6 VH pVII  .aa
MAEVQLLEEVNLVESGGGLVKPGGSLKLSCAASGFTFSSYAMSWVRQTPEKRLEWVASI

NNGGKIYYPDSVKGRFTISRDNARNILYLQMSSLRSEDTAMYYCVKRDSSVYDYAMDNW

GQGTSVTVSSGGGGSGMEQVADFDTIYQAMIQISVVLCFALGIIAGGQR*

SEQ ID NO 32  2h6 VH gVII  .seq
ATGGCCGAGGTGCAGCTGCTCGAGGAAGTGAATCTGGTGGAGTCTGGGGGAGGCTTAGT

GAAGCCTGGAGGGTCCCTGAAACTCTCCTGTGCAGCCTCTGGATTCACTTTTAGTAGTT
```

```
ATGCCATGTCTTGGGTTCGCCAGACTCCAGAGAAGAGGCTGGAGTGGGTCGCATCCATT

AATAATGGTGGTAAAATCTACTATCCAGACAGTGTGAAGGGCCGATTCACCATCTCCAG

AGATAATGCCAGGAACATCCTGTATCTTCAAATGAGCAGTCTGAGGTCTGAGGACACGG

CCATGTATTACTGTGTAAAAAGAGACAGTTCGGTCTACGACTATGCTATGGACAACTGG

GGTCAAGGAACCTCAGTCACCGTCTCCTCTGGTGGTGGTGGTTCTGGCATGGAGCAGGT

CGCGGATTTCGACACAATTTATCAGGCGATGATACAAATCTCCGTTGTACTTTGTTTCG

CGCTTGGTATAATCGCTG GGGGTCAAAGATAATAAGCTAGC

SEQ ID NO 33 92h2 VL pIX .aa
DIGLTQSPASLAVSLGQRATISCRASKSVSTSGYNYMHWYQQKPGQPPKLLIYLASNLA

SGVPARFSGSGSGTDFTLNIHPVEEEDAATYYCLYSREFPPWTFGGGTKLEIKRSGGGG

SMSVLVYSFASFVLGWCLRSGI TYFTRLMETSS*

SEQ ID NO 34 92h2 VL gIX .seq
GACATTGGGCTGACACAGTCTCCTGCTTCCTTAGCTGTATCTCTGGGGCAGAGGGCCAC

CATCTCATGCAGGGCCAGCAAAAGTGTCAGTACATCTGGCTATAATTATATGCACTGGT

ACCAACAGAAACCAGGACAGCCACCCAAACTCCTCATCTATCTTGCATCCAACCTAGCA

TCTGGGGTCCCTGCCAGGTTCAGTGGCAGTGGGTCTGGGACAGACTTTACCCTCAACAT

CCATCCTGTGGAGGAGGAGGATGCTGCAACCTATTACTGTCTGTATAGTAGGGAGTTTC

CTCCGTGGACGTTCGGTGGAGGCACCAAGCTGGAAATAAAACGTTCTGGCGGCGGCGGC

TCCATGAGTGTTTTAGTGTATTCTTTCGCCTCTTTCGTTTTAGGTTGGTGCCTTCGTAG

TGGCATTACGTATTTTACCCGTTTAATGGAAACTTCCTCATAATAAGCTAGC

SEQ ID NO 35 92h2 VH pVII .aa
MAEVQLQQSGPELKKPGETVKISCKTSGYSFTNYGMNWVKQAPGKGLKWMGWINTYTGE

PTYADDFRGRFAFSLATSASTAYLQIINLKNEDTATYFCETYDSPLGDYWGQGTTVTVS

SSSGGGGSGMEQVADFDTIYQA MIQISVVLCFALGIIAGGQR*

SEQ ID NO 36 92h2 VH gVII .seq
ATGGCAGAGGTCCAGCTTCAGCAGTCAGGACCTGAACTGAAGAAGCCTGGAGAGACAGT

CAAGATCTCCTGCAAGACTTCTGGATATTCCTTCACAAACTATGGAATGAACTGGGTGA

AGCAGGCTCCAGGAAAGGGTTTAAAGTGGATGGGCTGGATAAACACCTACACTGGAGAG

CCAACATATGCTGATGACTTCAGGGGACGGTTTGCCTTCTCTTTGGCAACCTCTGCCAG

CACTGCCTATTTGCAGATCATCAACCTCAAAAATGAGGACACGGCTACATATTTCTGTG

AAACCTATGATAGTCCCCTCGGGGACTACTGGGGCCAAGGCACCACGGTCACCGTTTCC

TCAAGTTCTGGTGGTGGTGGTTCTGGCATGGAGCAGGTCGCGGATTTCGACACAATTTA

TCAGGCGATGATACAAATCTCCGTTGTACTTTGTTTCGCGCTTGGTATAATCGCTGGGG

GTCAAAGATAATAAGCTA

SEQ ID NO 37 scFv 21H3-pIX .aa
MAEVQLLEVQLQQSGPVLVKPGGSVKMSCKASEYTLTSYLFQWVKQKSGQGLEWIGYIY

PYNGGTRYNEKFRGKATLTSDKSSNTAYLELSSLTSEDSAVYYCARSSMSDPGANWGPG

TLVTVSGGGGSGGGGSGGGGSDIQMTQSPSSLSASLGERVSLTCRASQEISGYLYWLQQ

KPDGTIKRLIYAASTLDSGVPKRFSGSRSGSDYSLTISSLESEDFADYYCLQYASYPRT

FGGGTKVEIKRAGGGGSMSVLVYSFASFVLGWCLRSGITYFTRLMETSS**AS

SEQ ID NO 38 scFv 21H3-gIX .seq
```

-continued

SEQUENCE LISTING

ATGGCCGAGGTGCAGCTGCTCGAGGTCCAGCTGCAACAATCTGGACCTGTGCTGGTAAA

GCCTGGGGGTTCAGTGAAAATGTCCTGCAAGGCTTCTGAATACACACTCACTTCTTATC

TTTTTCAGTGGGTGAAGCAGAAGTCAGGGCAGGGCCTTGAGTGGATTGGATATATTTAT

CCTTACAATGGTGGTACTCGGTACAATGAGAAGTTCAGAGGCAAGGCCACACTGACTTC

AGACAAGTCCTCCAACACAGCCTACTTGGAACTCAGCAGCCTGACCTCTGAAGACTCTG

CAGTCTATTACTGTGCAAGATCTAGTATGAGTGACCCCGGGGCTAACTGGGGCCCAGGG

ACTCTGGTCACTGTCTCTGGTGGTGGTGGTTCTGGCGGCGGCGGCTCCGGTGGTGGTGG

TTCTGATATCCAAATGACACAATCTCCATCCTCCTTATCTGCCTCTCTGGGAGAAAGAG

TCAGTCTCACTTGTCGGGCAAGTCAGGAGATTAGTGGTTACTTATACTGGCTTCAGCAG

AAACCAGATGGAACTATTAAACGCCTGATCTACGCCGCATCCACTTTAGATTCTGGTGT

CCCAAAAAGGTTCAGTGGCAGTAGGTCTGGGTCAGATTATTCTCTCACCATCAGCAGCC

TTGAGTCTGAAGATTTTGCAGACTATTACTGTCTACAATATGCTAGTTATCCTCGGACG

TTCGGTGGAGGCACCAAGGTTGAAATCAAACGGGCTGGCGGCGGCGGCTCCATGAGTGT

TTTAGTGTATTCTTTCGCCTCTTTCGTTTTAGGTTGGTGCCTTCGTAGTGGCATTACGT

ATTTTACCCGTTTAATGGAAACTTCCTCATAATAAGCTAGC

What is claimed is:

1. A filamentous phage encapsulating a genome encoding a fusion polypeptide and having said fusion polypeptide on a surface of said phage, wherein said polypeptide comprises an exogenous polypeptide fused to an amino terminus of a filamentous phage pVII or pIX protein.

2. The filamentous phage of claim 1 wherein said exogenous polypeptide is selected from the group consisting of an immunoglobulin heavy chain variable domain ($V_H$), an immunoglobulin light chain variable domain ($V_L$), a synthetic polypeptide and a single chain antibody (scFv).

3. The filamentous phage of claim 1 wherein said genome is pCGMT or pCGMT-1b having a nucleotide sequence shown in SEQ ID NO 19 or 20, respectively.

4. The filamentous phage of claim 2 wherein said scFv is scFv-21H3-pIX.

5. A library of filamentous phage particles wherein each phage particle is according to claim 1.

* * * * *